US006280958B1

(12) United States Patent
Rodkey et al.

(10) Patent No.: US 6,280,958 B1
(45) Date of Patent: Aug. 28, 2001

(54) RH BLOOD GROUP ANTIGEN COMPOSITIONS AND METHODS OF USE

(75) Inventors: L. Scott Rodkey; Marwan A. Yared; Kenneth J. Moise, Jr., all of Houston, TX (US)

(73) Assignees: Board of Regents, the University of Texas Systems, Austin; Baylor College of Medicine, Waco, both of TX (US)

( * ) Notice: Subject to any disclaimer, the term of this patent is extended or adjusted under 35 U.S.C. 154(b) by 0 days.

(21) Appl. No.: 09/488,157

(22) Filed: Jan. 20, 2000

Related U.S. Application Data

(62) Division of application No. 09/164,789, filed on Oct. 1, 1998, now Pat. No. 6,191,108, which is a division of application No. 08/715,173, filed on Sep. 17, 1996, now Pat. No. 5,840,585.

(51) Int. Cl.[7] .................................................. G01N 33/53
(52) U.S. Cl. ......................... 435/7.1; 435/7.21; 435/975; 436/520
(58) Field of Search ............................... 435/7.1, 7.9, 7.2, 435/7.21, 975; 430/520

(56) References Cited

U.S. PATENT DOCUMENTS

| | | |
|---|---|---|
| 5,387,511 | 2/1995 | Davidson et al. . |
| 5,840,585 | 11/1998 | Rodkey et al. . |

FOREIGN PATENT DOCUMENTS

| | | |
|---|---|---|
| 242716 | 2/1987 | (DE) . |
| WO 90/13032 | 11/1990 | (WO) . |

OTHER PUBLICATIONS

Agre and Cartron, "Molecular Biology of the Rh Antigens," *Blood*, 78:551–563, 1991.

Carter, "Preliminary Report on a Substance Which Inhibits Anti–Rh Serum," *Am. J. Clin. Path.*, 17:646–649, 1947.

Carter, "Rh Hapten: Its Preparation, Assay and Nature," *J. Immunol.*, 61:79–88, 1949.

Carter, "Preparation and Assay of a Red Cell Fraction of the Rh Factor," *Am. J. Clin. Path.*, 21:561–565, 1951.

Carter, "The Results in Clinical Use of Rh Hapten," *Am. J. Ob. Gyn.*, 102:447–450, 1968.

Carter et al., "Evaluation of Rh Hapten," *Am. J. Ob. Gyn.*, 72:655–659, 1956.

Carter and Lewis, "The Effects of Orally Administered Rh Hapten. A Study of 17 Cases," *Am. J. Ob. Gyn.*, 76:1286–1287, 1958.

Iyer et al., "Distribution of IgG Subtypes in Maternal Anti–D Sera and Their Prognostic Value in Rh Haemolytic Disease of the New–Born," *Acta Haematol.*, 88::78–81, 1992.

Masouredis, "Quantitative Studies of the $Rh_o$ (D) Antigenic Determinants of Gorilla Erythrocytes," *Transfusion* 11(5):270–280, 1971.

Moore et al., "Isolation of Membrane Components Associated with Human Red Cell Antigens Rh(D), (c), (E) and Fya," *Nature*, 295:529–531, 1982.

Moore et al., "Evaluation of monoclonal anti–Rh antibodies as reagents for blood grouping and for the identification of red cell membrane components associated with Rh antigen activity," *Revue Française de Transfusion et Immuno–hématologie*, 31(2):141–144, 1988.

Paradis et al., "Protective Effect of the Membrane Skeleton on the Immunologic Reactivity of the Human Red Cell $Rh_o(D)$ Antigen," *J. Immunol.*, 137:240–244, 1986.

Plapp et al., "Partial Purification Rh(D) Antigen from Rh Positive and Negative Erythrocytes," *Proc. Natl. Acad. Sci. USA*, 76:2964–2968, 1979.

Yokoi et al., "Isolation and Purification of $Rh_o(D)$ Antigen of Human Erythrocyte Membrane and Its Serological Property," *J. Exp. Med.*, 141:143–154, 1983.

Foreign Search Report dated Dec. 2, 1997.

Oellerich M., "Enzyme–Immunuoassay: A Review," *J. Clin. Chem. Clin. Biochem*, 22:895–904, 1984.

Sambrook, J. et al. "Molecular Cloning A Laboratory Manual," Cold Spring Harbor, New York: Cold Spring Harbor Laboratory Press, Second Edition, pp. 18.16–18.18, 1989.

Suyama et al. "Antibody produced against isolated Rh(D) polypeptide reacts with other Rh–related antigens'," Chemical Abstracts, vol. 109, Abstract No. 228190, *Blood*, 72(5):1622–1626, 1988.

*Primary Examiner*—Sheela Huff
(74) *Attorney, Agent, or Firm*—Fulbright & Jaworski LLP

(57) ABSTRACT

Disclosed are novel protein and peptide compositions comprising soluble and bound forms of immunologically-active blood group antigens including mammalian Rh antigens. In preferred embodiments methods for the isolation and purification of serologically-active human Rh antigens such as D, c, C, E, and e are disclosed. Also disclosed are methods for the adsorption of immunologically-active Rh antigens to solid supports. Diagnostic kits, methods, and devices for the detection of Rh antibodies in clinical and non-clinical samples are also disclosed. Devices, compositions and methods for the isolation, purification and quantitation of anti-Rh antibodies from solution are also provided.

12 Claims, 20 Drawing Sheets

RH BLOOD GROUP ANTIGEN COMPOSITIONS AND METHODS OF USE

Figure 1:
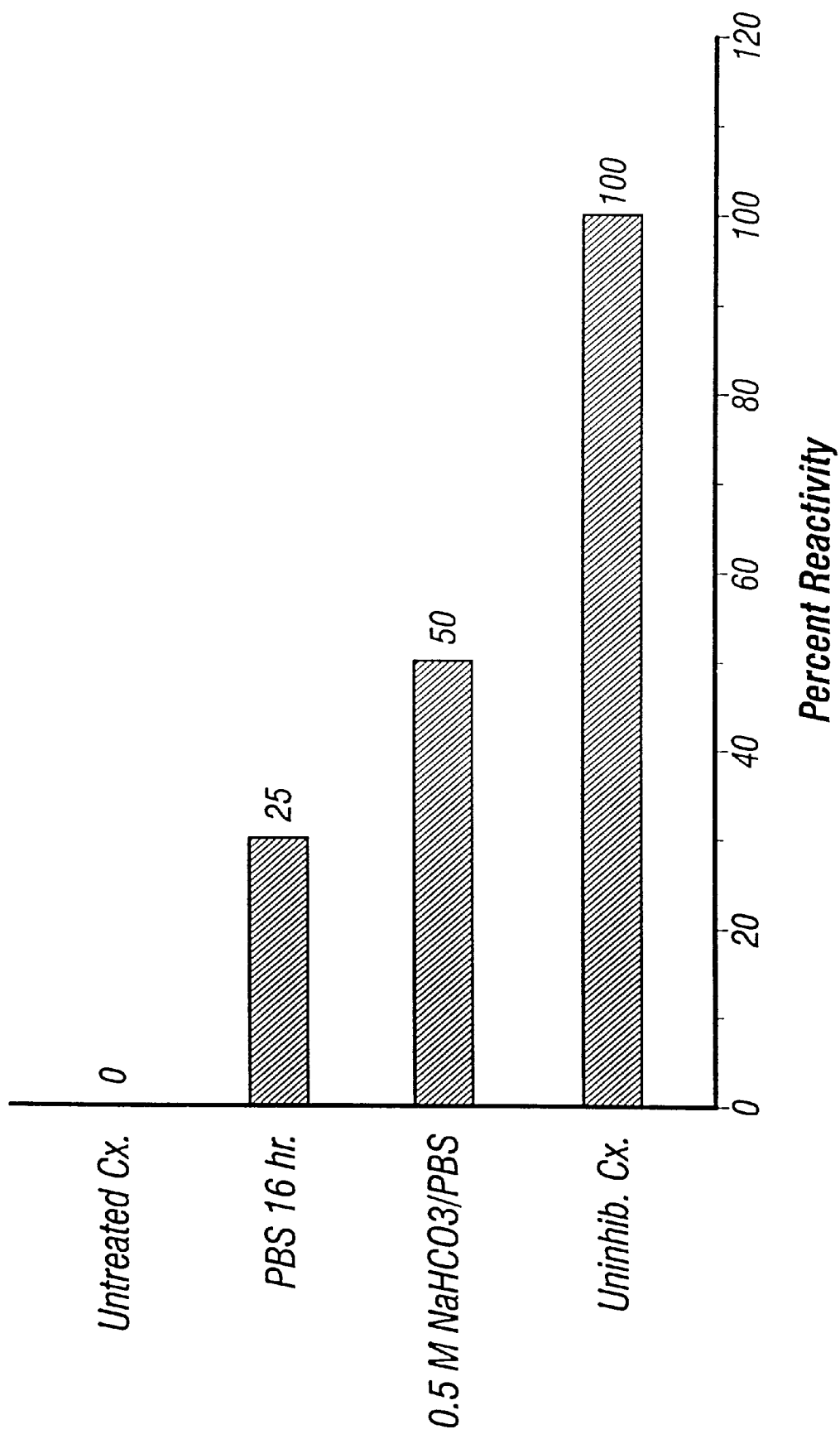

This application is a divisional of co-pending application Ser. No. 09/164,789, filed Oct. 1, 1998, now U.S. Pat. No. 6,191,108, which is a divisional of application Ser. No. 08/715,173, filed Sep. 17, 1996 now U.S. Pat. No. 5,840,585.

1. BACKGROUND OF THE INVENTION

1.1 Field of the Invention

The present invention relates to the fields of protein chemistry and hematology. More particularly, the invention discloses novel compositions comprising solid-phase, ie., bound, forms of immunologically-active Rh antigen. Also disclosed are diagnostic kits and devices for the detection and quantitation of Rh antibodies in clinical and non-clinical samples. In another aspect, the invention relates to devices, compositions and methods for the isolation, identification, quantitation, and purification of anti-Rh antibodies from solution.

1.2 Description of the Related Art

1.2.1 Rh Antigens

The Rh blood group system is one of the most complex polymorphisms in humans. Human red blood cells (RBCs) may be subdivided into $Rh^+$ and $Rh^-$ groups according to the presence or absence of the major Rh blood group antigen, Rhesus D ($Rh_o$ D) (Cartron and Agre, 1993). Several genes have been implicated as encoding the major Rh antigen epitopes, D, C, c, E, and e, while a host of others are speculated to be involved in the determinants of a host of rare alleles.

Rh antigens, including $Rh_o$ D, are carried on an integral membrane protein which has a molecular weight of approximately 30 kDa (Moore et al., 1982; Gahmberg, 1982; 1983). This protein has been implicated in the molecular adhesion of the submembranous cytoskeleton to the erythrocyte cell membrane (Ridgwell et al., 1984), and persons lacking the proteins exhibit Rh Deficiency Syndrome, accompanied by varying degrees of hemolytic anemia (Marsh, 1983).

Paradis et al. (1986) demonstrated that the presence of the cytoskeleton in isolated $Rh_o$ D antigen preparations served as a protective effect on the immunologic activity of the Rh antigen.

1.2.2 Hemolytic Disease of the Newborn (HDN)

The RBC antigen system in humans is the basis for the disease called Hemolytic Disease of the Fetus/Newborn. This disorder is manifested when an $Rh^-$ woman becomes pregnant by an $Rh^+$ man. The fetus is statistically likely to be $Rh^+$ and during gestation or at birth, $Rh^+$ fetal RBC can enter the maternal circulation and the woman then has a high probability of developing an anti-Rh antibody response against the transferred RBC. In subsequent pregnancies, the IgG form of the antibody crosses the placenta and enters the fetal circulation where it binds to fetal $Rh^+$ RBC and thereby causes them to be rapidly removed from circulation in liver and spleen. The first child is rarely affected since the mother has not yet developed the antibodies, but all subsequent fetuses are at risk for disease if the mother is not appropriately treated.

The current treatment for this condition is strictly preventive. The strategy is to attempt to keep the woman from initially developing anti-Rh antibodies. This is done by administering 300 $\mu$g of an immunoglobulin (Ig) preparation that contains anti-Rh antibodies at 28 weeks of gestation and again within 72 hr of birth. This is highly effective in preventing the disease when the patient comes in early for prenatal care. Unfortunately, large numbers of women do not obtain proper prenatal care for various reasons and go on to develop strong anti-Rh immune responses. For these women, in utero transfusion of the fetus under ultrasound guidance is the only current treatment available for high-risk cases when the woman has previously developed a strong immune response against the Rh antigen. Because eighty-five percent of the Caucasian population is $Rh^+$, a considerable number of women and their offspring are potentially at risk for contracting the disease.

1.2.3 Attempts To Isolate Active Solid-Phase Rh Antigen Have Failed

Unfortunately, attempts to isolate active Rh antigen have been disappointing, and no successful attempts at preparing bound forms of the antigen have been reported. Indeed, a definitive review (Agre and Cartron, 1991) reported that Rh antigenic activity was lost after membranes are solubilized or transferred onto immunoblot membranes, and most biochemical methods therefore actually kill the antigenic activity that identifies and defines the Rh antigen.

Moore et al. (1982) and Plapp et al. (1979) each reported isolation of small amounts of Rh antigen after affinity chromatography of deoxycholate solubilized RBC. Plapp et al. (1979) solubilized the cells in deoxycholate, added the mixture to an affinity column made of immobilized anti-Rh antibodies and eluted the bound fraction. The resulting eluate was active in inhibition of a reaction between $Rh^+$ RBC and antibody. Disappointingly, however, extracts from both $Rh^+$ and $Rh^-$ cells inhibited the reaction, with the authors postulating that Rh antigen was merely "hidden" in $Rh^-$ cells.

That conclusion, however, was disproved when modem molecular biology methods conclusively showed that Rho (D) antigen is not present in $Rh^-$ cells (Agre and Cartron, 1991), and that the Rh antigen polypeptides had molecular weights of between 28 and 32 kDa (Agre and Cartron, 1991). Clearly the 7 kDa polypeptide reported by Plapp and coworkers could not be the Rh antigen polypeptide.

Moore et al. (1982) surface-labeled RBC with $^{125}I$, reacted the labeled cells with anti-Rh antibodies, washed the cells and dissolved them in deoxycholate. This was passed over a protein A-Sepharose column and complexes were isolated after elution. Although they were successful in detecting Rh antigen in acrylamide gel separations of eluted complexes by autoradiography, the amount of Rh protein isolated by their method was too low to provide definitive analysis of Rh protein. In fact, the quantities were so small, that no inhibition assays could be performed to ascertain the activity and integrity of the isolated protein.

A report in 1986 suggested that minor amounts of Rh antigen could be isolated in soluble form (Paradis et al., 1986), but unfortunately, this method, too, provided a limited quantity of Rh antigen, and the preparation was contaminated with cytoskeleton components. Attempts by workers in the field to repeat the method for isolation of large-quantities of active Rh antigen were unsuccessful, as were attempts to couple the soluble form of the antigen to various solid-phase supports and maintain antigenicity of the preparation when adsorbed to solid-phase matrices such as ELISA plates, nitrocellulose, plastic beads, Sepharose, etc. using standard methodologies.

1.2.4 Unavailability of Solid-Phase Rh Antigen Has Limited Hematology

The unavailability of solid-phase (or bound) Rh antigen compositions, and the lack of ability of using contemporary immunoassay methodologies such as ELISA and solid-phase antigen assays have confounded the field of hematology for many decades.

Because of these limitations, and because no assays for anti-Rh antibodies exist except for time-consuming, cumbersome, non-quantitative RBC agglutination assays, the fields of hematology, obstetrics and neonatology are severely lacking in this important regard. The shortcomings of the present methodologies in the area are many.

First, the results are reported as a titer (ie. the highest dilution of the serum in question that gives a standard degree of agglutination). It is commonly understood in the field that titer results are highly subjective depending on who reads the result. Variations of ±1 tube are accepted variations due to this subjectivity. Further, it is commonly known that a given serum can be given to two different individuals or two different laboratories and the reported titers can be dramatically different. Even if reporting of titers was absolute, the doubling dilutions used would mean that reported results potentially have almost 100% error inherent.

For example, suppose that 5 $\mu$g/ml antibody would yield an agglutination titer of 1:32. This would mean that the patient would need to have 10 $\mu$g/ml to yield a titer of 1:64. Thus, an amount of antibody of 9.5 $\mu$g/ml would be reported as a 1:32 titer because only 2-fold dilutions are made. The higher the antibody concentration, the greater the discrepancy becomes, i e., if the titers were reading 200 versus 400 $\mu$g/ml, a concentration of 390 that is interpreted as 200 is greatly under reported by titering.

1.3 Deficiencies in the Prior Art

The isolation of active Rh antigen polypeptides, and in particular, the $Rh_o$ D antigen-bearing polypeptide, in large quantity has eluded scientists for more than half a century. That it has not been possible to isolate, store, and immobilize antigenically- (or serologically-) active blood group antigens, and in particular Rh antigen, represents a significant limitation in the medical arts. Because of the unavailability of large amounts of antigenically-active blood group antigen proteins, it has been impossible to develop improved assays and methods for identifying, isolating and purifying specific antibodies which recognize these antigens. Likewise, the unavailability of bound forms of serologically-active blood group antigens has prevented the development of affinity matrices comprising blood group antigens such as Rh antigens, ELISA methodologies specific for these antigens, and devices for the inline purification and removal of anti-blood group antibodies from solution. Because of the impossibility of isolating antigenically-active Rh antigens in quantity using conventional methods, development of such methods and compositions have never been available. Moreover, because no method currently exists for the isolation of antigenically-active Rh antigens, and in particular D antigen, all current analytical procedures in hematology must rely on the availability of intact RBCs. Standard blood bank practice relies on doing agglutination assays using defined RBC and patient serum.

During clinical management of previously alloimmunized patients, critical treatment decisions often depend on a combination of symptoms and laboratory results. Knowledgne of the level of anti-D antibody can be crucially important in determining the management strategy for such patients. Unfortunately, there is a wide variation in the results of the doubling dilution titers reported by laboratories. A recent surbey of laboratories was done by the College of American Pathologists to determine the uniformity of results reported for a single standard anti-D serum (College of American Pathologists, 1996). In the survey, 1641 participants were given the same anti-D serum and were asked to report titers. Titer scores varied widely with results ranging between titers of 1:2 and 1:2048. Titers of 1:32 or 1:64 were reported by 59.5% of participants and a titer range of 1:16 to 1:128 was reported by 86% of participants. Thus, 14% of laboratories reported titers below 1:16 or above 1:128 for the identical sample. Such results dramatically illustrate the well-known variability of the doubling dilution agglutination titer method of anti-Rh antibody measurement currently in use in the medical community and underline the urgent need for development of a quantitative assay method for Rh blood group antigens, and D antigen in particular.

Therefore, what is lacking in the prior art is the availability of antigenically-active blood group antigens, and in particular Rh antigens such as the D antigen. Also lacking are methods for the isolation and maintenance of such antigens in serologically-active forms both soluble and bound. What is needed is the availability of quantitative analyses and methods for the determination of Rh antigens in solution, identification and quantitation of anti-Rh antibodies, and methods and diagnostic kits for the ready determination of both antigen and antibodies specific for blood group antigens such as Rh antigens, and in particular D antigen. Such methods and compositions would provide a revolutionary advance in the medical arts, particularly in the areas of hematology, blood banking, transfusion medicine, obstetrics, and neonatology, and would permit fabrication of devices and apparatus useful for the isolation and purification of anti-Rh antibodies from solution. Such apparatus would be particularly useful in treatment of disorders such as hemolytic disease of the newborn.

2. SUMMARY OF THE INVENTION

The present invention overcomes these and other deficiencies in the prior art by providing novel methods and compositions comprising serologically- (antigenically-) active blood group antigens, and in particular, Rh antigens including the D antigen, which may be adsorbed to a variety of solid supports including ELISA microtiter plates, plastic and glass beads, coverslips, sepharose, agarose, and other solid-phase antigen-presenting supports. Methods are disclosed for the preparation, storage, and assay of antigenically-active blood group antigens such as the Rh antigens in both soluble and bound forms. The invention also provides compositions and methods comprising anti-blood group antibodies, and in particular, anti-Rh antibodies, such as anti-D antibodies, as well as methods for isolation, identification, and quantitation of these antibodies. Other aspects of the invention are apparatus and devices for the isolation of anti-Rh antibodies from solution, and in particular, methods and compositions for the isolation and removal of anti-D antibodies from a mammal such as a human. Such methods and devices find particular utility in the removal of anti-Rh antibodies from the blood of a pregnant female, and in the treatment and prevention of HDN and other related fetal disorders.

2.1 Methods for Stabilizing Antigenically-Active Forms of Blood Group Antigens

The inventors have demonstrated that the serologic integrity of Rh antigen extracts can be protected from the detrimental effects of salt buffers by incorporating amphoteric buffers in the isolation protocol. Suitable amphoteric buffers which may be used to successfully store and manipulate active Rh antigen include, but are not limited to, those solutions which have amphoteric properties. Such buffers are well-known in the art, and include, among others, WRA, glycine, HEPES, MOPS, Bis-Tris, Alanine, and Acetate. The buffers described by Good and Izawa (1972) are also contemplated to be useful in the practice of the invention.

In an illustrative embodiment, the inventors have utilized the amphoteric buffer WRA to isolate, store, and manipulate active Rh antigen. The buffers are useful in pH ranges of 1 to 6, and are most preferred in the range of from about pH 2 to about pH 7, although higher and lower pH ranges may be contemplated to be useful for certain applications. Concentrations of from about 0.1% to about 5% for WRA, glycine, HEPES, MOPS, Bis-Tris, and alanine are most preferred, as are concentrations of from about 0.01 M to about 1.0 M for acetate.

The bound (or solid-phase) antigen is very stable in amphoteric buffers and retains serologic activity for extended periods of time. Using the ampholyte/glycine buffer, ELISA assays have now been done successfully with both the human and the rabbit forms of the Rh antigen. Preferred buffers include ampholytes as those described in U.S. Pat. No. 3,485,736, incorporated herein by reference, although any such amphoteric buffer is contemplated to be useful in the preparation, storage and adsorption of the antigens disclosed herein.

In a preferred embodiment, the amphoteric composition WRA, a novel buffer formulated by the inventors, has been shown to be useful in the practice of the methods disclosed herein. The formulation of WRA buffer is disclosed in Example 1. Alternatively, the ampholyte buffers as disclosed in U.S. Pat. No. 3,485,736 (incorporated herein by reference) are equally useful in the practice of the present invention.

2.2 Compositions Comprising Solid-Phase Blood Group Antigens

In a preferred embodiment the present invention provides serologically-active blood group antigens immobilized onto a solid support or substrate. One such family of preferred antigens is the Rh antigens, and a most preferred Rh antigen is the Rh D antigen. The solid support or substrate may be, but is not limited to, matrices, columns, chromatographic media, glass or plastic surfaces, acrylic beads, beaded agarose, Sepharose, coverslips, microscope slides, test tubes, vials, bottles, ELISA supports, and the like. When desired, the antigenic polypeptides may be adsorbed onto such media either by hydrophobic interaction, or by active crosslinking of the protein antigen(s) to the solid support or substrate by cyanogen bromide, oxirane, p-nitrophenyl chloroformate activation or by any other suitable means known to those of skill in the art.

The solid support may be in the form of an apparatus or device which comprises a chamber, one or more inlet ports, one or more outlet ports, and a matrix within the chamber to which the antigenically-active form of the protein or peptide is adsorbed or chemically crosslinked. In an illustrative embodiment, the inventors adsorbed Rh D antigen to t-butyl HIC beads (Bio-Rad), passed a solution containing anti-D antibodies over the column, and removed such antibodies from solution via the binding of the anti-D antibody to the D antigen adsorbed to the column. Methods are also provided for washing such a column, device or apparatus to remove contaminating materials, and then subsequently eluting the bound antibody from the antigen matrix using eluants such as chaotropic reagents.

2.3 Novel Methods for Low-pH Adsorption of Antigens to Solid Matrices

The inventors have devised a methodology incorporating two non-obvious steps that permit the efficient adsorption of Rh antigens to a solid support or substrate. The invention provides novel compositions comprising such solid-phase active Rh antigens, and provides methods and devices for solid-phase active Rh antigens, and in particular, the adsorption of Rh antigen to glass and plastic beads and to ELISA plates, microtiter dishes, slides, and other substrata.

The first requirement for preservation of Rh antigenicity when Rh polypeptides are adsorbed to solid supports is to do all manipulations involving the antigen in salt-free organic buffers particularly organic amphoteric buffers). The second requirement is that the antigen adsorption be performed at low pH (a condition that normally denatures most protein antigens). In a surprising finding, the inventors have demonstrated that adsorption of the antigen under conditions where the pH was 1 to 6 was preferred, with a pH range of 2 to 5 being more preferred, and a pH of 2.4 to 4.5 being most preferred for adsorption of the antigenically-active protein to a solid support.

2.4 Methods for Isolation of Anti-Rh Antibodies

Methods are disclosed and claimed for isolating antibodies specific to blood group antigens from solution using the compositions, devices, and apparatus disclosed herein. In particular, these methods are applicable to the isolation of Rh-specific antibodies from solution. In a preferred embodiment, methods for isolating anti-D antibodies from solution is provided. Preferably the solution is a biological solution, such as blood, serum, plasma, monoclone culture supernatant, tissue culture supernatant, bacterial culture supernatant, cell fluid, lymph, cerebrospinal fluid, synovial fluid, or any other biological sample where the presence of one or more blood group antibodies are suspected. In preferred embodiments, the solution is a biological solution from a mammal, and in particular a human or a rabbit, although the inventors contemplate that other animals such as bovines, equines, porcines, goats, and the like may also provide a source for the particular solution to be used in practice of the invention. Preferably the animal is human, and more preferably, the animal is a pregnant female.

By contacting the blood of the mammal with a solid-phase Rh antigen composition of the invention, anti-Rh antibodies may be removed from the solution by adsorption to the antigenically-active bound Rh antigen. In a most preferred embodiment, anti-D antibodies are removed from solution such as human blood, plasma, or serum using a device, composition, or apparatus comprising an antigenically-active form of the D antigen.

To facilitate adsorption of the antibody to the antigen, the solid-phase antigen composition may be incubated in the presence of a solution containing anti-Rh antibodies with agitation for an appropriate time period to permit adsorption of the antibody to the antigen-matrix.

In an alternate embodiment, the contact can be made in the form of a column connected to one or more pumping devices, such as a peristaltic pump, for example, to enhance the flow rate of the antibody-containing solution past the solid-phase support comprising the antigen. The contact step may be repeated two, three, four or even more than four times with further depletion of antibodies from the solution at each step. In a most preferred embodiment, an in-line affinity matrix column apparatus is contemplated for the isolation and removal of anti-Rh antibodies from the circulatory system of a human.

2.5 Devices and Apparatus for Isolation of Antibodies from Solution

The invention discloses and claims apparatus and devices which comprise the novel antigenically-active protein antigens of the present invention. These apparatus and devices are provided for the isolation of antibodies specific for the bound antigens from solution. In particular, devices are provided for the removal of Rh antibodies from the circulatory system of an animal. Most preferably, the animal is a pregnant human female whose circulatory system contains anti-D antibodies.

The availability of a serologically-active solid-phase antigen also provides a means for specific antibody purification so that dramatically smaller doses of anti-Rh antibodies could be used for therapies which currently rely on the whole globulin fraction of pooled high-titered anti-Rh sera. Polyclonal antibodies are known to be much more active in diagnostic assays than the available monoclones. The devices and apparatus of the present invention represent novel and useful means for removing specific antibodies from solution, and in particular for lowering the titer of anti-Rh antibodies in the circulatory system of an animal, and in particular, a woman with a high anti-Rh titer.

In conjunction with the preceding method, the inventors also contemplate the formulation of apparatus and devices for the in-line removal of anti-(blood group antigen) antibodies from solution, and particularly from the bloodstream of a pregnant human female. In preferred embodiments, such antibodies are anti-Rh antibodies, with anti-D antibodies being most preferred. In a general sense the devices comprise a chamber having inlet and outlet ports, and contained within such a chamber, a composition comprising an immunologically-active immobilized blood group antigen. The device is then used to adsorb the anti-(blood group antigen) antibodies from solution passed through the device and over the matrix. Such devices may optionally comprise one or more pumps to facilitate the passage of solution over the matrix. Single or multiple inlet and outlet ports may be fitted onto the chamber depending upon the particular application. Such ports may optionally have fittings such as Leur-Lok collars for attachment of tubes, hoses, or syringes fitted with a Leur-Lok connection.

The manufacture of in-line devices for the purification of components from whole blood, serum, plasma, lymph, synovial fluid, etc. is well-known in the art. Such devices are useful in applications relating to plasmapheresis. In this process, plasma is separated from blood cell components and passed through a filtration mechanism.

Absorbed antibody matrices such as Sepharose, cellulose, nylon, glass, acrylic, or other plastic, or inert resins, beads, fibers, etc. are all contemplated to be within the scope of this application when employed for the removal of antibodies from solution using the novel Rh antigen compositions disclosed herein.

In a preferred embodiment, the use of t-butyl HIC beads coated with Rh antigen in an inline immunoadsorbant filter under conditions of room temperature, pH 7.2 to 7.4 for a period of from about 2 to about 4 hr is contemplated to be useful for the removal of anti-Rh antibodies from a biological fluid such as plasma.

The inventors contemplate that any such device which comprises an antigen-bound to a matrix could be used in an in-line format with a plasmapheresis machine to remove antibodies from plasma of women with high levels of anti-Rh antibodies. The plasma would circulate through the device, anti-Rh antibodies would bind to the antigen-matrix, and the plasma eluate would then be reinfused into the patient. This would be particularly useful in quickly lowering the anti-Rh titer of a pregnant patient if the fetus is in danger from the presence of such circulating antibodies. The inventors anticipate that the in-line removal of antibodies from maternal circulation could be used to deplete anti-Rh antibodies making in utero transfusion unnecessary.

In a general sense, an apparatus of the present invention comprises a chamber with an inlet port and an outlet port, and an immobilized antigenically-active blood group antigen composition contained within the chamber. The chamber may be of any shape, although cylindrical chambers are preferred. The antigens which may be bound to the solid support include one or more blood group antigens such as a D antigen, a c antigen, a C antigen, an e antigen, an E antigen, an A antigen, a B antigen, or an F antigen, or any other of the blood group antigens disclosed herein or known to those of skill in the art.

Optionally, the apparatus can further comprise one or more pumps. As described herein, the solid support may be of any suitable material to which one or more antigenically-active blood group antigens may be adsorbed. Preferred matrices include, but are not limited to, glass, plastic, acrylate, methylmethacrylate, Sepharose, agarose, nylon, fiber, or glass wool supports. In a preferred embodiment, the protein or peptide is immobilized under conditions of low pH, with a pH range of about pH 6 to about pH I being preferred and a pH range of from about pH 2.4 to about pH 4.5 being most preferred. The proteins or peptides may be immobilized in the presence of an amphoteric or zwitterionic buffer such as EDTA, WRA, MOPS, HEPES, glycine, alanine, Bis-Propane or Bis-Tris. Typically, the concentration of buffer will be on the order of from about 0.01% to about 5%, or more preferably, from about 1% to about 4%.

One such device contemplated by the inventors to be useful in the practice of the invention is a column such as the FDA-approved device for inline absorption of total IgG antibodies known as a Prosorba® column (IMRE Corp., Seattle, Wash.). This column is approximately 3"D×4"H and is filled with a matrix of Silica to which is coupled staphylococcal Protein A. This column is used to absorb all IgG from plasma, regardless of specificity. Although it is currently approved only for use in patients with Idiopathic Thrombocytopenic Purpura (ITP, an autoimmune disease in which antibodies to platelets or antibodies to foreign antigens that are adhered to platelets destroy the platelets), modification of this column using the novel blood group antigens disclosed herein would provide a device for the specific removal of particular blood group antigens from solution.

Figure 18:
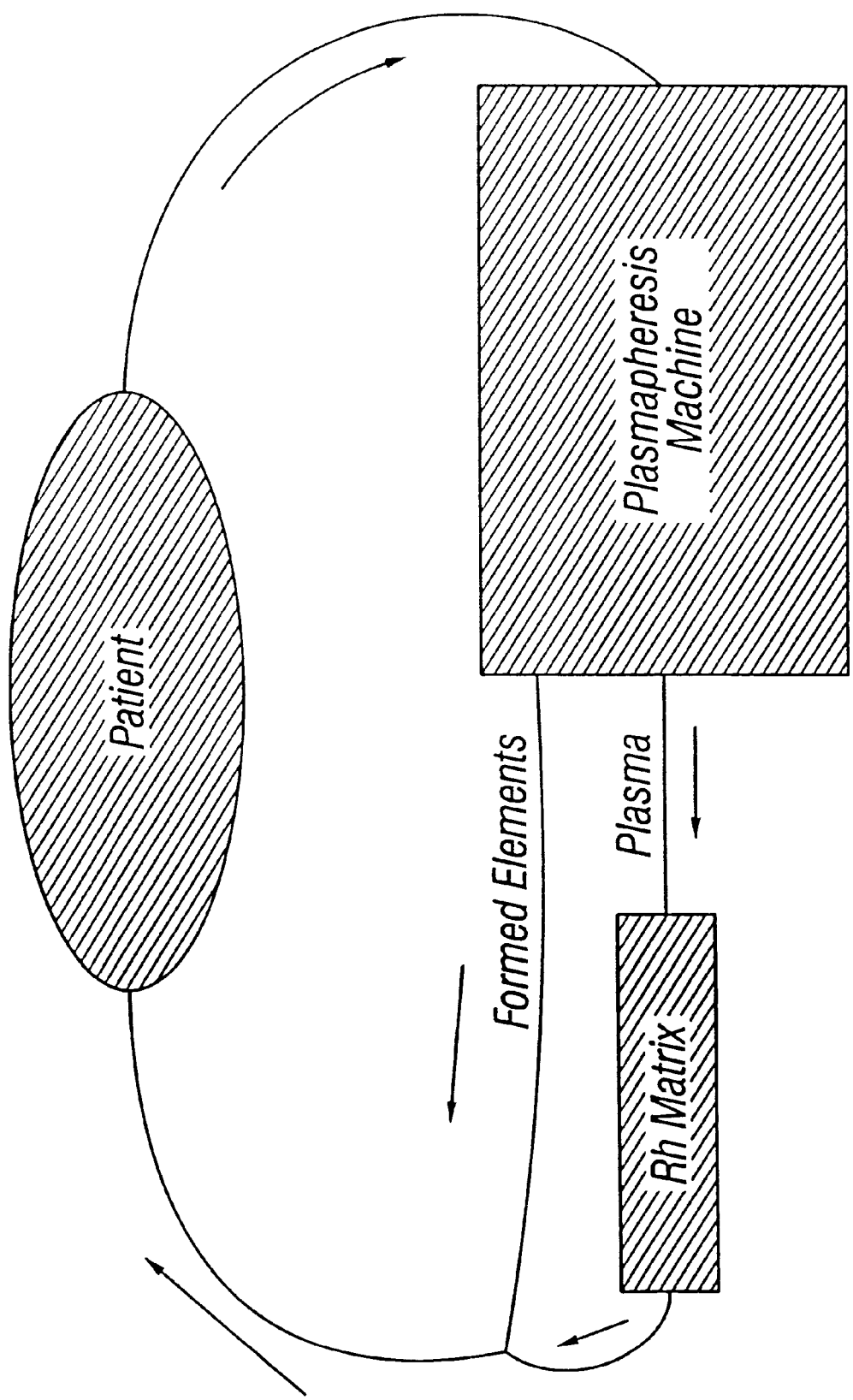

The inventors propose a modification of such a column for specific removal of anti-blood group antibodies, and in particular anti-Rh antibodies using the novel antigens of the present invention. While the capacity of such a blood group antigen-specific column may differ from a native Prosorbae column, one of skill in the art would be able to modify the column and formulate a blood group antigen-specific column in a similar fashion. Such a column could contain a single blood group antigen, or a combination of two or more blood group antigens. An example of this column and the general schematic for its use in isolating antibodies from the circulatory system of an animal is illustrated in FIG. 18 and FIG. 19.

In an illustrative embodiment of this aspect of the invention, the inventors created an apparatus which consisted of a 50 ml column containing beads coated with the rabbit homolog of the human Rh D antigen ($Rh_{RABBIT}$ F). From this device, the inventors isolated 90.2 mg of purified anti-F antibody. When the size of the column was increased to 60 ml of $Rh_{RABBIT}$ F-coated beads, the inventors isolated 145.4 mg of purified anti-F anti-body from a solution passed over the column.

Figure 19A:
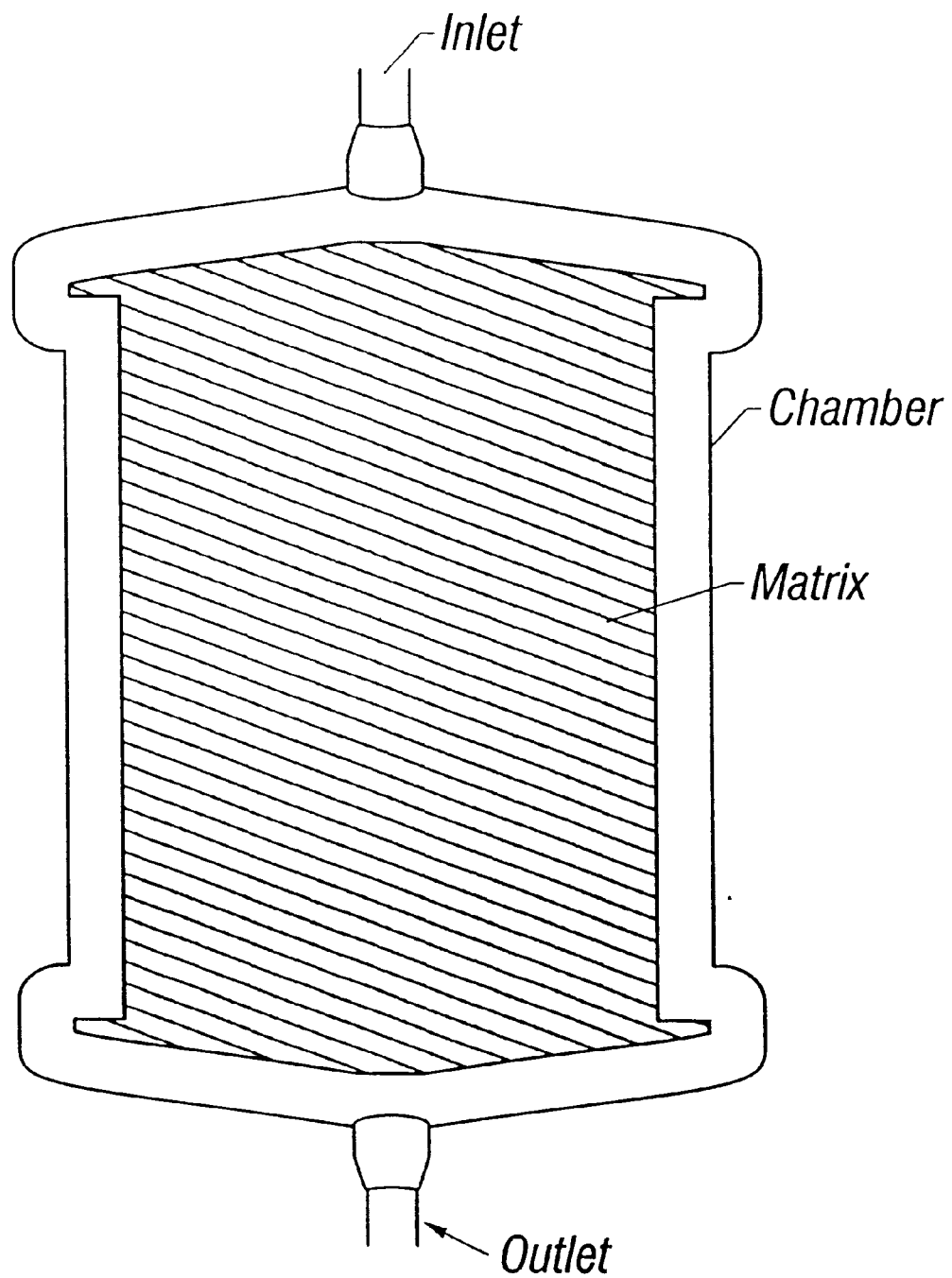
Figure 19B:
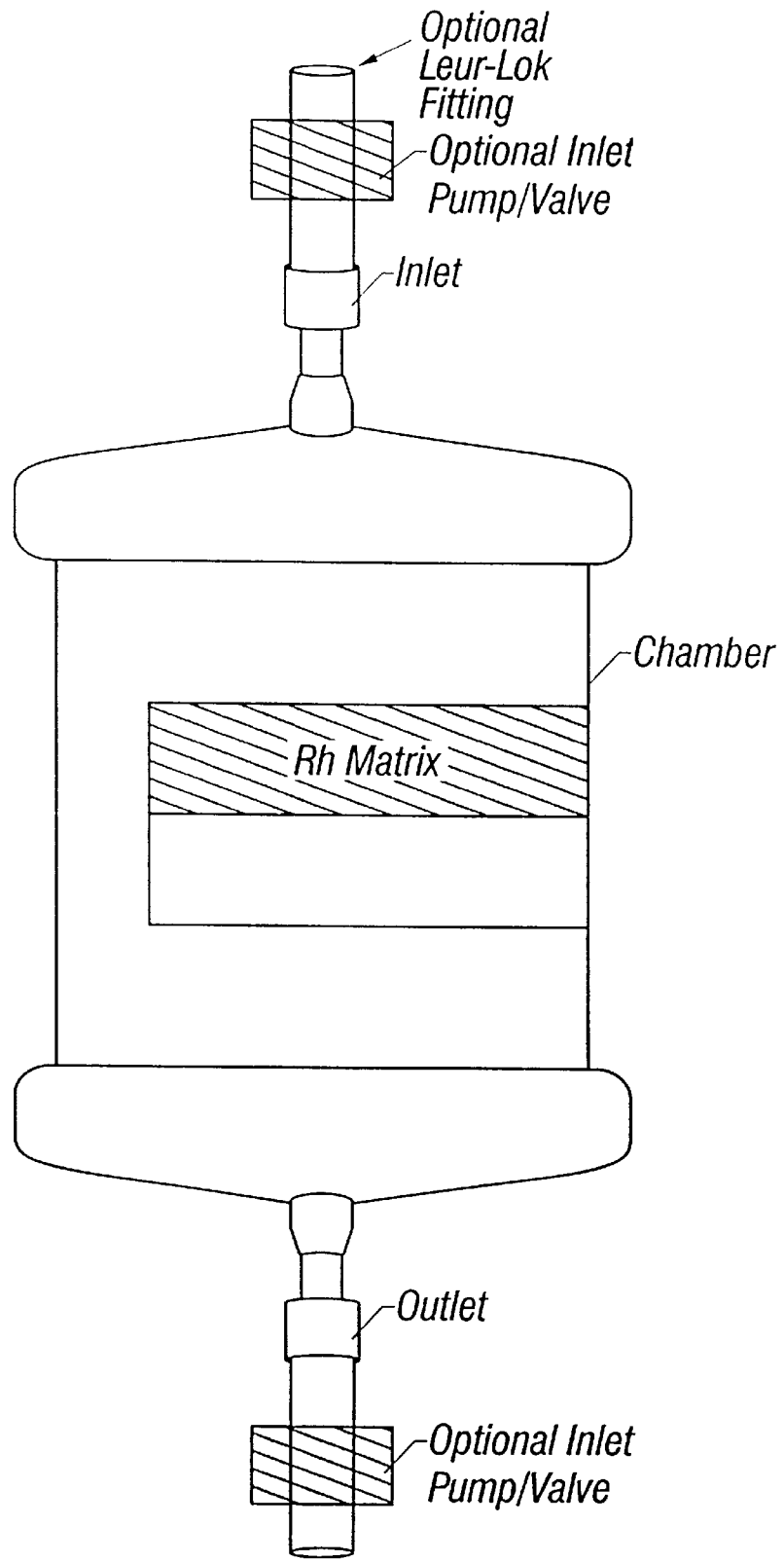

The inventors contemplate that a variety of solid phase supports comprising adsorbed or covalently crosslinked antigenically-active forms of blood group antigens such as the Rh antigens, and in particular the D antigen could be fashioned in devices similar to these illustrated in FIG. 19A and FIG. 19B to provide the specific removal of Rh antigen-specific antibodies from solution, and particularly, as an inline means of removing antibodies from the circulatory system of an animal. One such inline means is illustrated schematically in FIG. 18 which depicts a varation of plasmapheresis, a method well-known to those of skill in the art for separating plasma from the circulatory system of an animal. Incorporation of a device or apparatus of the present invention into such a method would facilitate an ex vivo isolation and removal of antibodies directly from the bloodstream of an animal using one or more serologically-active protein antigens coupled to a matrix contained within a device such as that illustrated in FIG. 19A and FIG. 19B.

2.6 Compositions and Methods for Quantitative Assay of Blood Group Antigens and Antibodies The invention provides active Rh antigen for use in ELISAs and related quantitative methodologies. The availability of active solid-phase Rh antigen now permits the development of quantitative diagnostic protocols and kits comprising the compositions disclosed herein. By utilizing the Rh antigen to coat ELISA plates, prequantified specifically purified antibodies may be used to create a standard curve for quantitation of Rh antigens which may now be prepared in large quantity through conventional or recombinant methods that are well-known to those of skill in the art. Patient sera may then be diluted as in conventional agglutination assays, with the results being quantitated using a standard curve in conventional units (typically $\mu$g/ml, e.g.). Such methods are well-known in the art, and are routinely performed for antigens such a growth hormones, etc. using ELISA, RIA, or related techniques which are also known to those of skill in the art. In an important aspect of the invention, the availability of the active Rh antigen compositions disclosed herein, now extends the use of ELISA and RIA methodologies for use in detection and quantitation of anti-Rh antibodies. Prior to the present invention, no such tests had been available to clinicians and hematologists.

One aspect of the invention is a composition comprising an isolated and purified antigenically-active blood group antigen protein or peptide. Such an antigen is preferably a mammalian antigen such as that derived from a human or rabbit. In preferred embodiments, the antigen is an Rh antigen or a rabbit homolog of a human Rh antigen such as a D antigen, a c antigen, a C antigen, an e antigen, an E antigen, an A antigen, a B antigen, or an F antigen. In an important aspect of the invention, the protein or peptide is antigenically-active under conditions of low pH such as in the range of from about pH 6 to about pH 1. More preferably, the pH is from about pH 2.4 to about pH 4.5. In sharp contrast to the prior art in which antigenically-active Rh antigens were stable in solution for only short periods of time, the antigen compositions of the present invention are stable for significantly longer periods of time, such as e.g., for periods of time from at least 4 hours to as much as 192 hours or more.

The compositions of the invention may further comprise an amphoteric or zwitterionic buffer such as EDTA, WRA, MOPS, HEPES, glycine, alanine, Bis-Propane or Bis-Tris, and the like. Typically, the buffer is present at a concentration of from about 0.01% to about 5%.

The peptide antigen compositions may be soluble, or alternatively they may be immobilized onto a solid support such as a glass, plastic, acrylate, methylmethacrylate, Sepharose, agarose, nylon, fiber, or glass wool substrate or the like. Immobilized peptide antigen compositions are particularly contemplated to be useful in the formulation of petri dishes, test tubes, vials, microscope slides, ELISA plates, microtiter dishes, culture plates and the like to which it is desirable to adsorb or chemically crosslink the novel peptide antigens. Such immobilized antigen compositions are particularly preferred for the formulation of immunoaffinity columns and similar matrices. Once immobilized, the peptide antigens may be maintained in solution, or alternatively, may be dried and stored in dry form for extended periods of time. In preferred embodiments, the inventors have shown the antigen compositions to be stable for at least 192 hrs without loss of antigenic activity. Such compositions find particular utility in the fomulation of immunodetection reagents, diagnostic kits, and blood group antigen/antibody assays.

2.7 Diagnostic Kits, Immunodetection Reagents, and Assays

The present invention provides methods, compositions and kits for screening samples suspected of containing Rh antigen polypeptides or Rh antigen-related polypeptides, or cells producing such polypeptides. Said kit can contain a nucleic acid segment encoding an Rh antigen polypeptide, or an anti-Rh antibody. The kit can contain reagents for detecting an interaction between a sample and a nucleic acid or antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatography media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the Rh antigen peptides of the present invention may be employed to detect antibodies having reactivity therewith, or, alternatively, antibodies prepared in accordance with the present invention, may be employed to detect Rh antigen or Rh antigen-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either an Rh antigen peptide or an Rh antigen-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of Rh antigen or Rh antigen-related proteins or peptides and/or antibodies in a sample. Samples may include cells, cell supernatants, cell suspensions, cell extracts, enzyme fractions, protein extracts, or other cell-free compositions suspected of containing Rh antigen peptides. Generally speaking, kits in accordance with the present invention will include a suitable Rh antigen peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.8 ELISAs and Immunoprecipitation Methods

ELISAs may be used in conjunction with the invention. In an ELISA assay, proteins or peptides incorporating Rh antigenic sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins, cells must be solubilized into detergent micelles. Nonionic salts are preferred, since other agents such as bile salts, precipitate at acid pH or in the presence of divalent cations.

In an alternative embodiment the antibodies of the present invention are useful for the close juxtaposition of two antigens. This is particularly useful for increasing the localized concentration of antigens, e.g. enzyme-substrate pairs.

The generic protocol is to coat the wells with a sufficient amount of Rh antigen (e.g., about 50 to about 75 $\mu$l or more Rh antigen) for a sufficient period of time (e.g., from about 4 to about 16 hr), at a suitable incubation temperature (e.g., from about 4° C. to about 37° C., with room temperature being most preferred). The plates are then washed and may be blocked at this point by adding from about 50 to about 200 $\mu$l of blocking agent and incubating for periods of a few minutes to about 4 hr at a temperature of from about 4° C.
to about 37° C. The plates may then be washed again one or more times, and the sample containing the antibody is applied. If a radiolabeled antibody or antigen is used, then the sample may be washed and then counted directly using a protocol such as in a RIA.

Alternatively, in the case of ELISAs, the assay procedure typically involves the addition of an appropriate substrate at a suitable concentration for detection either with or without added peroxide (e.g., when using HAP) and subsequent incubation period (usually from a few minutes to about 4 hr at a temperature ranging from about 4 to about 37° C.), depending upon the particular protocol used. Reagents are added to stop the enzymatic reaction (i.e., 100 $\mu$l of 2 M $H_2SO_4$). The plates are then read on an ELISA reader at a wavelength appropriate for the enzyme-substrate system being used. Such protocols are well-known to those of skill in the art, and may be modified as necessary to include the novel antigen composition of the present invention.

This same assay can be used to determine serum levels of each of the four subclasses of IgG. There are some recent papers that suggest that severity of symptoms of HDN may be due to differences in the quantitative levels of IgG subclasses (Iyer et al., 1992; Garner et al., 1995). For such an assay, specific conjugates would be used that are each specific for one of the subclasses. There are murine Mab available specific for each of the four human IgG subclasses. These would be used for such assays after conjugation to appropriate enzyme.

This same assay is used for creation of a standard curve. For this, a preparation of specifically purified anti-Rh antibody is used that has been precisely quantitated using spectrophotometry or other method. Aliquots of this preparation that have been accurately diluted are put into the ELISA protocol and a standard curve is generated by plotting antibody concentration in $\mu$g/ml versus OD. The particular wavelength used for optical density measurements will depend upon the particular substrate being assayed.

Once the standard curve has been generated for a given batch of Rh antigen, patient samples are read on the linear part of the curve and extrapolated to $\mu$g/ml of antibody contained in whole serum.

2.9 Compositions for Western Blots and Related Immunoblot Methods

The antigen compositions of the present invention will find great use in immunoblot or Western blot analysis. The novel Rh antigens may be used directly as standards (e.g., as a positive control) in Western analyses wherein one desires to determine the presence of Rh antigens in a test sample. Alternatively, the novel Rh antigens may be used to isolate, quantitate, purify, and concentrate anti-Rh antibodies which may also be used in Western analyses as a high-affinity primary antibody reagent for the identification of Rh proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies directed against the anti-blood group antibody are considered to be of particular use in this regard.

2.10 Compositions for Determining Blood Group Antigen Epitopic Core Sequences

In one aspect, the present invention provides for the first time the ability to isolate and purify substantial amounts of Rh protein, and to store and manipulate this protein without significant loss of antigenic activity. Prior to the discovery by the inventors that significant long-term storage and stabilization of the blood group antigens such as the D antigen could be facilitated by using amphoteric buffers such as WRA, glycine, and the like, it was not possible to isolate or maintain either in solution or in bound form significant quantities of antigenically-active blood group antigens. Likewise, prior to the surprising finding by the inventors that conditions of low pH could be used to bind antigenically-active forms of Rh antigen to solid supports, it was not possible to prepare such compositions. Thus it was not previously possible to obtain significant quantities of these antigens to characterize antigenic domains, to determine epitopic core sequences, or to prepare mutated, truncated, or otherwise altered amino acid sequences defining a whole or a portion of an Rh antigen protein.

However, in light of the teaching of the instant specification, it is now possible to isolate such proteins and to characterize antigenic domains and epitope sequences therefrom. Thus, the invention discloses and claims Rh proteins, Rh protein derivatives, and Rh-derived peptide compositions, free from total cells and other peptides, which comprise a whole or a portion of a purified Rh antigen protein or peptide which incorporates an epitope that is immunologically cross-reactive with one or more anti-Rh antibodies.

As used herein, the term "incorporating an epitope(s) that is immunologically cross-reactive with one or more anti-Rh antibodies" is intended to refer to a peptide or protein antigen which includes a primary, secondary or tertiary structure similar to an epitope located within an Rh antigen polypeptide. The level of similarity will generally be to such a degree that monoclonal or polyclonal antibodies directed against the Rh antigen polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Rh antigen immunodominant epitopes, and/or their functional equivalents, is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these “epitopic core sequences” may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic Rh antigen-derived peptides will provide advantages in certain circumstances, for example, in the preparation of vaccines or in immunologic detection assays. Exemplary advantages include the ease of preparation and purification, the relatively low cost and improved reproducibility of production, and advantageous biodistribution. Previously, it was not possible to isolate significant amounts of Rh protein, to maintain such protein in solution for extended periods of time, to prepare peptide fragments derived from Rh antigen, or to identify or characterize the epitope(s) present on the protein. The availability of Rh antigen protein in quantity provides an opportunity to prepare immunogenic Rh compositions which maintain their serologic integrity for extended periods of time.

It is proposed that particular advantages of the present invention may be realized through the preparation of synthetic peptides which include modified and/or extended epitopic/immunogenic core sequences which result in a “universal” epitopic peptide directed to Rh antigen and Rh antigen-related sequences. These epitopic core sequences are identified herein in particular aspects as hydrophilic regions of the Rh antigen polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is “complementary” to, and therefore will bind an antigen binding site. Additionally or alternatively, an epitopic core sequence is one that will elicit antibodies that are cross-reactive with antibodies directed against the peptide compositions of the present invention. It will be understood that in the context of the present disclosure, the term “complementary” refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of the Rh peptide in the amphoteric buffers disclosed herein, the Rh peptide compositions may be readily stored in an amphoteric buffer such as WRA, glycine, Bis-Tris, MOPS, HEPES, Tris, etc. for fairly long periods of time if desired, e.g., up to six months or more, without appreciable degradation or loss of antigenic activity. Where extended aqueous storage is contemplated it will generally be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use. The Rh antigen may be stored in a lyophilized state either by itself, or alternatively, may be bound to a solid support prior to drying. The inventors contemplate that the antigen may be stored in a dry form either bound to beads, matrices, or prepared onto an ELISA plate or other suitable support depending upon the particular application for which it will be used for periods of time extending from weeks to months.

2.11 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons listed in Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (4.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

2.12 Methods for Producing Anti-Blood Group Antigen Antibodies

An important aspect of the invention relates to the generation of antibodies which are reactive against either a whole or portion of an Rh antigen peptide isolated as described herein. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antiserum from that immunized animal. A wide range of animal species can be used for the production of antiserum. Typically the animal used for production of antiserum is a rabbit, a mouse, a rat, a hamster, a guinea pig or a goat. Because of the relatively large blood volume of rabbits, a rabbit is a preferred choice for production of polyclonal antibodies. Alternatively, antiserum may be obtained from a human subject.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of antibody is obtained, the immunized animal can be bled and the serum isolated and stored, and/or the animal can be used to generate mAbs. mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Rh antigen protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used for fusion, as are known to those of skill in the art (Goding, pp. 65–66, 1986; Campbell, pp. 75–83, 1984). For example, where the immunized animal is a mouse, one may use P3-X63/Ag8, X63- Ag 8.653, NS1/1.Ag 4 1, Sp210-Ag14, FO, NSO/U, MPC-11, MPC11-X45GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Arninopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants-(after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted, cloned, and propagated indefinitely to provide mAbs. The cell lines may be exploited for mAb production in two basic ways. Hybridoma cells can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.12 Means for the Removal of Anti-Rh Antibodies from Solution

Another aspect of the present invention concerns methods for removing anti-Rh antibodies from solution. In a general sense, the method involves the immobilization of a serologically-active blood group antigen, such as an Rh antigen, as disclosed herein, and passing a solution containing antibodies reactive thereto over the immobilized antigen under conditions which permit the binding of specific antibodies to the bound antigen. Such a process may comprise a solid-phase matrix onto which one or more antigenically-active blood group antigen proteins have been fixed. In an illustrative embodiment, the matrix comprises plastic beads (10 to 100 $\mu$m in diameter) such as Bio-Rad MacroPrep hydrophobic interaction chromatography (HIC) beads, and in particular t-butyl HIC beads, although the inventors contemplate a variety of similar beads or matrices may be used to immobilize the active antigen. In practice, any suitable matrix to which the antigen may be adsorbed, fixed upon, or crosslinked to is desirable, as long as the serologic integrity and antigenic property of the Rh antigen is maintained. The method for removing antibodies from solution in a general sense comprises passing a solution suspected of containing Rh antibodies over the matrix under conditions which allow the formation of antigen-antibody (immune) complexes. The efficiency of the process may be monitored by comparing the titer of Rh antibodies in solution before and after the solution is passed over the matrix, or alternatively, the antibodies which were bound to the matrix may be eluted from the column or matrix and collected.

The solution from which antibodies may be removed include, but are not limited to, physiological fluids, such as blood, lymph, serum, synovial fluid, cerebrospinal fluid, plasma, culture supernatant, tissue culture supernatant, monoclone culture supernatant, etc. or any other biological fluid in which the presence of Rh antibodies is suspected. Preferably the solution is blood, and more preferably, mammalian blood. In a preferred embodiment, the inventors contemplate the method to be useful in the in-line removal of anti-Rh antibodies from the bloodstream of a human female which is suspected of containing Rh antibodies. In general, the offspring of a female with an anti-Rh titer in excess of 1:2 who is pregnant by an $Rh^+$ male are considered to be at risk for HDN if the offspring are also $Rh^+$. The first child from such a pregnancy may be at risk for HDN if there was significant transplacental bleeding early in pregnancy, and if the mother developed anti-D antibodies as a result of the first pregnancy. Subsequent offspring from such a pregnancy are also at risk for HDN. This is critical, because such fetuses may suffer severe clinical problems due to the maternal antibodies attacking and destroying fetal RBCs. In fact, such conditions may lead to severe anemia in the fetus, and in some cases fetal intrauterine death due to a depletion of fetal RBCs.

In a preferred embodiment, a method of purifying an Rh antibody is disclosed. The method generally comprises contacting a sample suspected of containing an antibody with an immobilized antigen under conditions effective to bind the antibody and subsequently eluting the antibody from the immobilized antigen.

A method of removing an Rh antibody from a biological fluid is also disclosed and claimed in the invention. The method generally comprises contacting such a fluid with an immobilized Rh antigen under conditions effective to bind the antibody to the antigen.

2.13 Definitions

The current literature uses two nomenclatures to express genetic and seologic information on the human red blood cell Rh blood group antigen system. The Rh-Hr terminology derives from the work of Wiener (1943) who believed that the immediate gene product is a single entity called an agglutinogen. According to Wiener's concept, each agglutinogen was characterized by numerous individual serologic specificities called factors, each of which was recognized by its own specific antibody.

The CDE terminology was introduced by British workers Fisher and Race (1948) and it reflected the concept that individual genes determined each antigen. The same letter designation was used for both the gene and the gene product in the Fisher-Race system, except that, by convention, the symbols for genes were always listed in italics. Both nomenclatures have remained in use today, although recent molecular biology advances have shown that each major antigenic specificity in the Fisher-Race nomenclature system in encoded by a distinct gene, and that five genes, D, C, c, E, and e encode five phylogenetically-related, but distinct, peptide antigens which are termed D, C, c, E, and e.

Thus, as used throughout this specification, a blood group antigen is intended to mean any protein or peptide antigen present on the surface of a red blood cell. For example, an Rh blood group antigen is intended to mean a D antigen, a C antigen, a c antigen, an E antigen, an e antigen, or any other related Rh antigen. A blood group antigen is also intended to mean a $Rh_o$, rh'hr', hr" or rh" antigen according to the earlier nomenclature of Wiener. A blood group protein is intended to mean any protein or peptide present on the surface of a red blood cell that contains within its sequence one or more antigenic regions to which anti-blood group antigen antibodies will bind. An Rh protein or peptide is intended to mean a D protein or peptide, a C protein or peptide, a c protein or peptide, an E protein or peptide, an e protein or peptide, or any other related Rh blood group protein or peptide. A blood group protein is also intended to mean an $Rh_o$, rh'hr', hr" or rh" protein or peptide according to the earlier nomenclature of Wiener. A blood group antigen is also intended to mean an amino acid sequence which defines a portion or a whole of a gene product derived from a D gene, a C gene, a c gene, an E gene, or an e gene. Moreover, a blood group protein is also intended to mean any mammalian-derived antigen which is homologous to any of these human antigens. Such antigenic proteins include, but are not limited to, the rabbit A, D, and F antigens.

Likewise, an anti-(blood group antigen) antibody is intended to mean an antibody which specifically recognizes and binds to an antigen present on the surface of a red blood cell. An anti-Rh antibody is intended to mean an antibody such as an anti-D antibody, an anti-C antibody, an anti-c antibody, an anti-E antibody, an anti-e antibody, or any other related Rh antibody. An anti-(blood group antigen) antibody is also intended to mean an antibody which specifically recognizes and binds to an antigen present on the surface of a red blood cell such as an anti-$Rh_0$ antibody, an anti-rh' antibody, an anti-rh" antibody, an anti-hr' antibody, or an anti-hr" antibody following the nomenclature of Wiener. Similarly, an anti-(blood group protein) is also intended to mean any mammalian-derived antibody which is specific for any protein or peptide antigen which is homologous to a human blood group antigen. Such antibodies include, but are not limited to, the rabbit anti-A, anti-D, and anti-F antibodies.

In addition to the two major blood group systems (ABO and Rh) the following blood group antigen systems are known, and are also considered to be within the scope of the present invention: MNSsU, P1, Lutheran, Kell, Lewis, Duffy, Kidd, Diego, Cartwright, Dombrock, Colton, Scianna, $Xg^a$, I/i, Augustine, Cromer, $En^a$, Gerbich, Gregory, Holley, jacobs, Joseph, Lngereis, $Ok^a$, Vel, Chido, Rodgers, Cost-Stirling, York, Knops-Helgeson, McCoy, John Milton Hagen, Ahonen, Batty, Biles, Bishop, Box, $Chr^a$, Dantu, Froese, Good, Griffiths, Heibel, Hey, Hov, Hunt, Jensen, $Jn^a$, Lewis II, Livesey, Mitchell, Moen, Orriss, Peters, Radin, Redelberger, Reid, Rosennlund, Swann, Torkiidsen, Traversu, Webb, Wright, Wulfsberg, and Bg. Each of these systems may have several antigens and phenotypes, but all have at least one known antigen (e.g., Lewis has two antigens and 3 phenotypes).

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Aliquots of human D⁺ antigen were dialyzed overnight vs. 0.1 M PBS or against 0.5 M $NaHCO_3$ overnight followed by 4 hr dialysis vs. PBS. The samples were then used to inhibit a reaction between monoclonal anti-D and trypsin-treated D⁺ human RBC in a slide agglutination assay. Untreated Cx is the original antigen preparation in EDTA buffer and the Uninhib. Cx is the antibody mixed with RBC with only PBS added in place of inhibitor.

Figure 2:
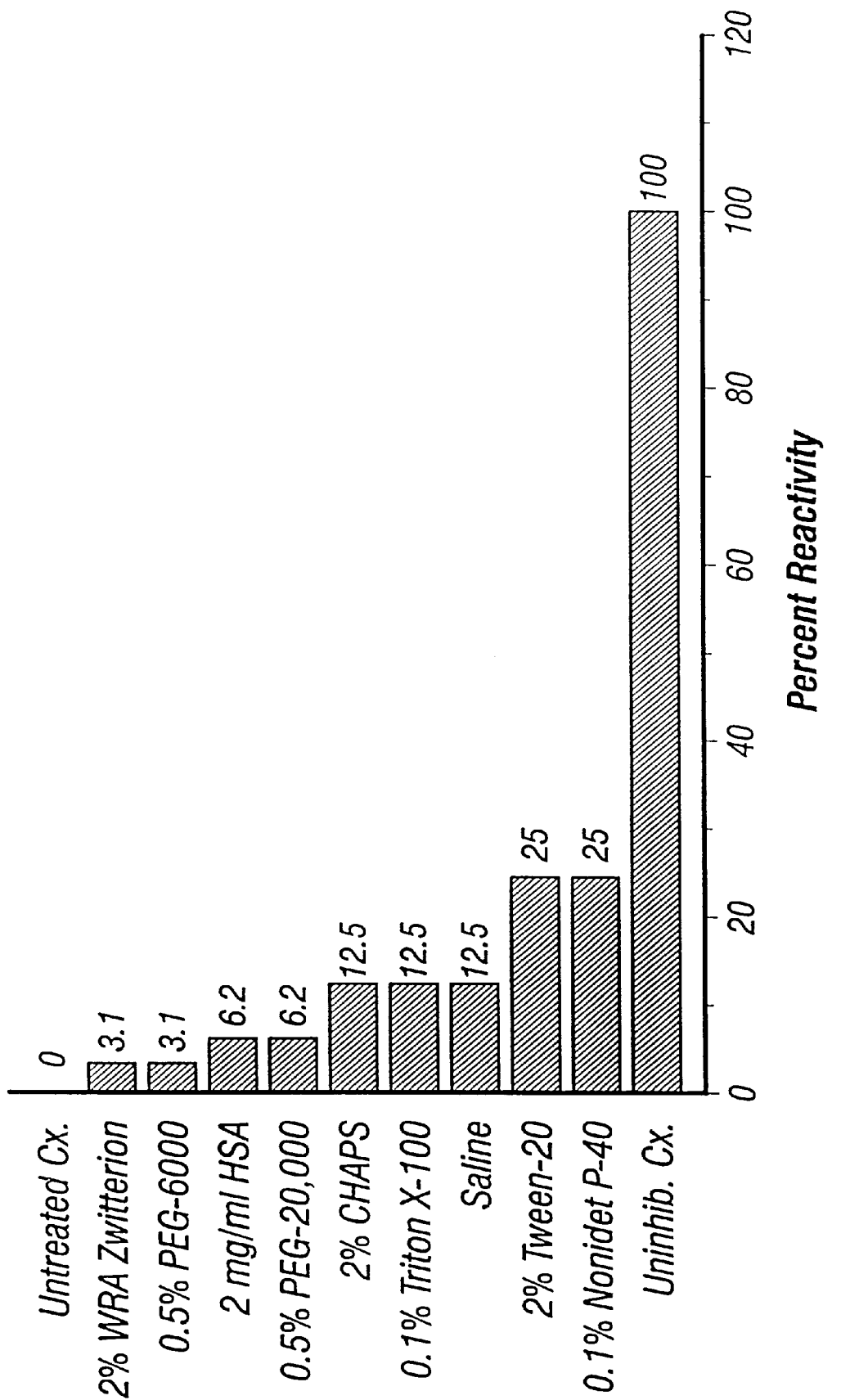

FIG. 2. Aliquots of $Rh_{RABBIT}$ antigen were put in the presence of the indicated final concentrations of several proteins, ampholytes, detergents, zwitterions, etc. for 16 hr. And the inhibitory capacity of the mixture on an RBC slide agglutination reaction was measured. EDTA Buffer was used as the Untreated Cx. and the Uninhibited Cx. was made using only EDTA buffer as a volume control.

Figure 3:
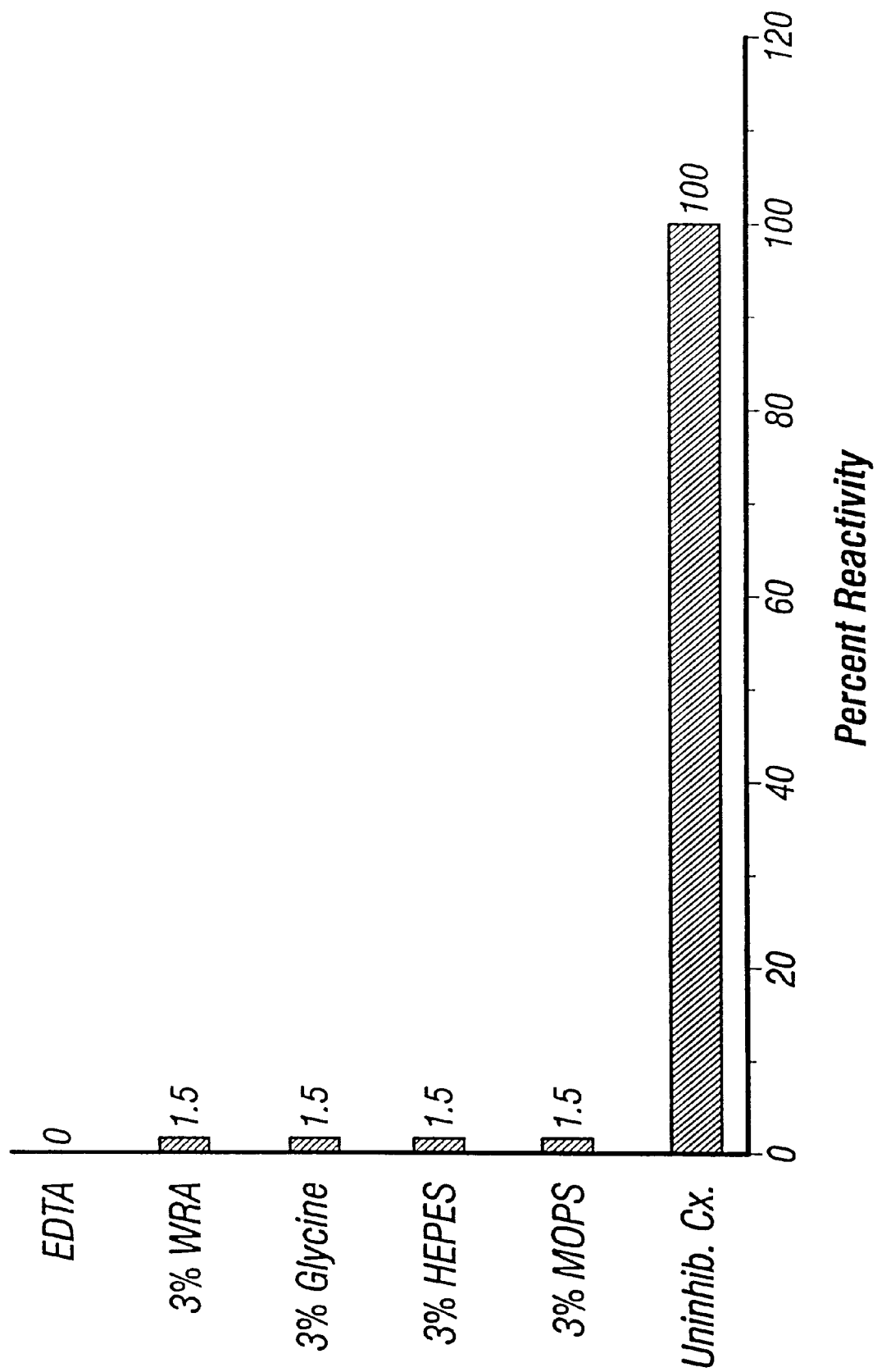

FIG. 3. Aliquots of $Rh_{RABBIT}$ antigen were put in the presence of the indicated final concentrations of amphoteric buffers for 16 hr. and the inhibitory capacity of the mixture on an RBC slide agglutination reaction was measured. $Rh_{RABBIT}$ antigen in EDTA buffer was used as the EDTA control (top) and EDTA buffer as a volume control in an uninhibited control (bottom) was used.

Figure 4:
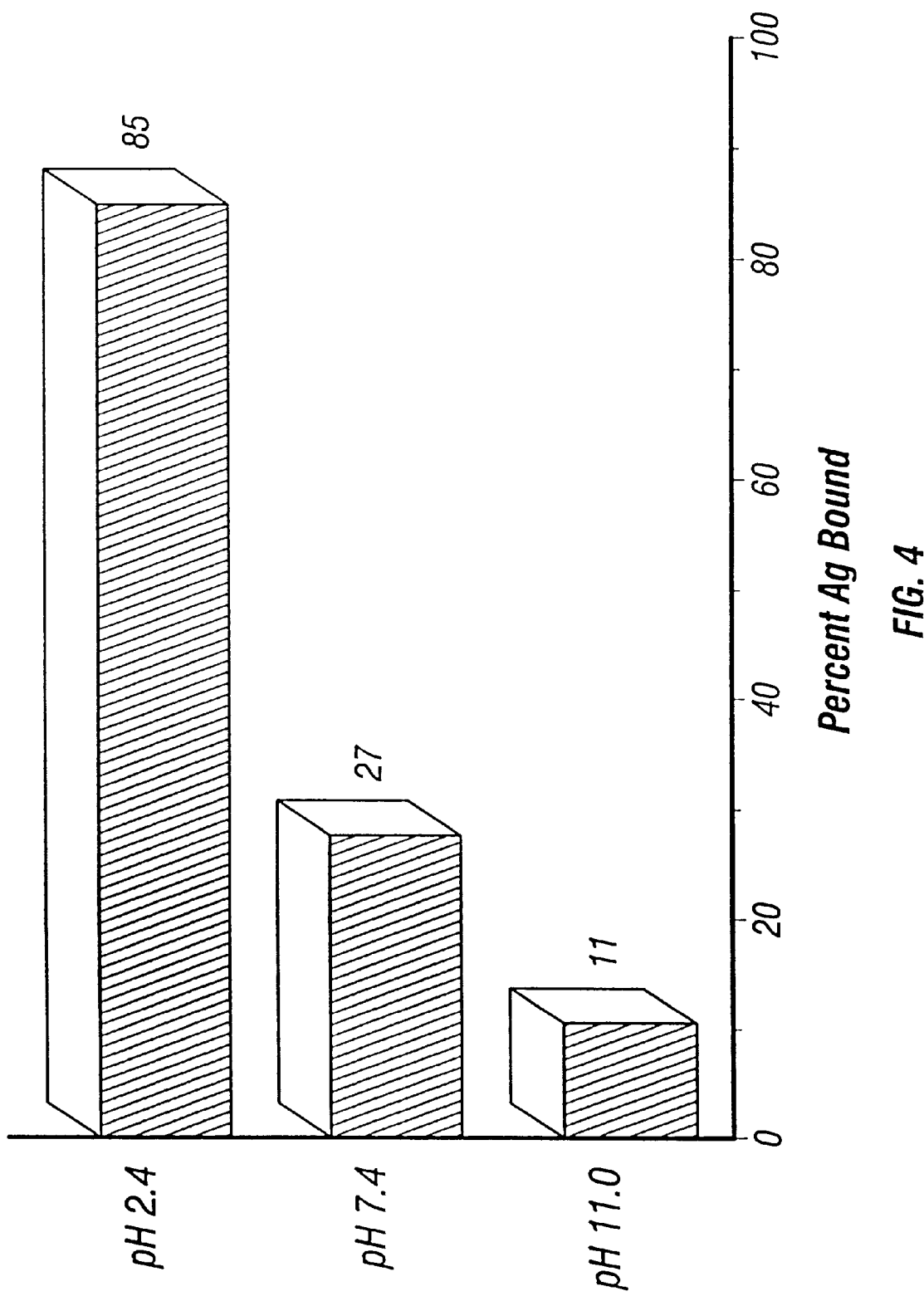

FIG. 4. $Rh_{RABBIT}$ antigen in EDTA buffer was made to final concentration of 0.2 M glycine by adding dry glycine. The pH of one aliquot was then dropped to 2.4 with 6 M Hcl, a second aliquot was raised to pH 11 using ethylenediamine, and the pH of a third aliquot was raised to pH 7.4 also using ethylenediamine. One volume of each aliquot of Bio-Rad HIC t-butyl beads was mixed with two volumes of $Rh_{RABBIT}$ antigen and incubated over-night with agitation. The $OD_{280}$ of the supernatant and washes was read in a spectrophotometer and compared to the total $OD_{280}$ of antigen added to beads to determine the amount of antigen bound to beads.

Figure 5:
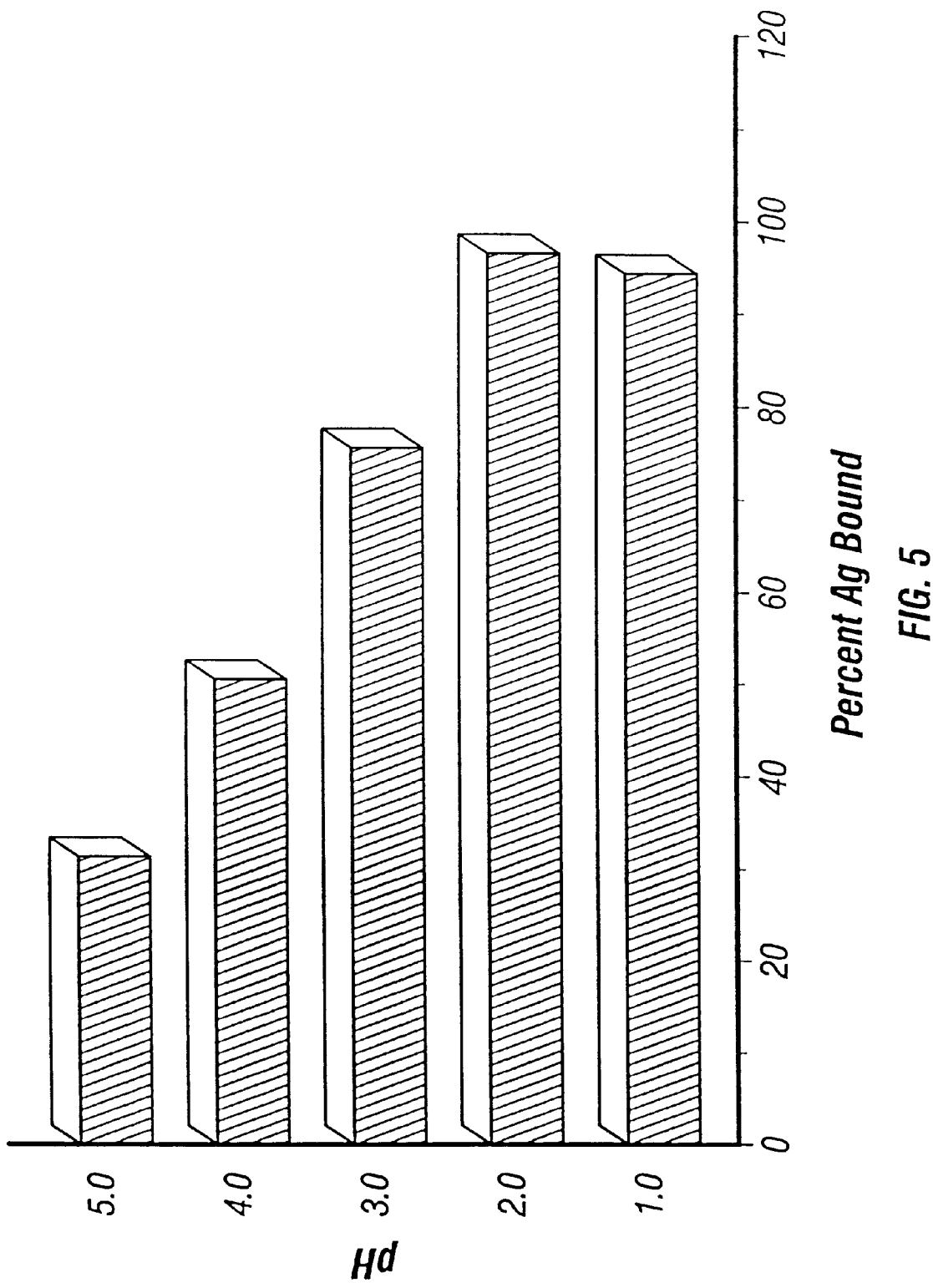

FIG. 5. $Rh_{RABBIT}$ antigen in EDTA buffer was mixed with aliquots of beads as described in FIG. 4 with the pH adjusted to the values shown. After incubation and washing, the $OD_{280}$ of supernatants was determined as in FIG. 4.

Figure 6:
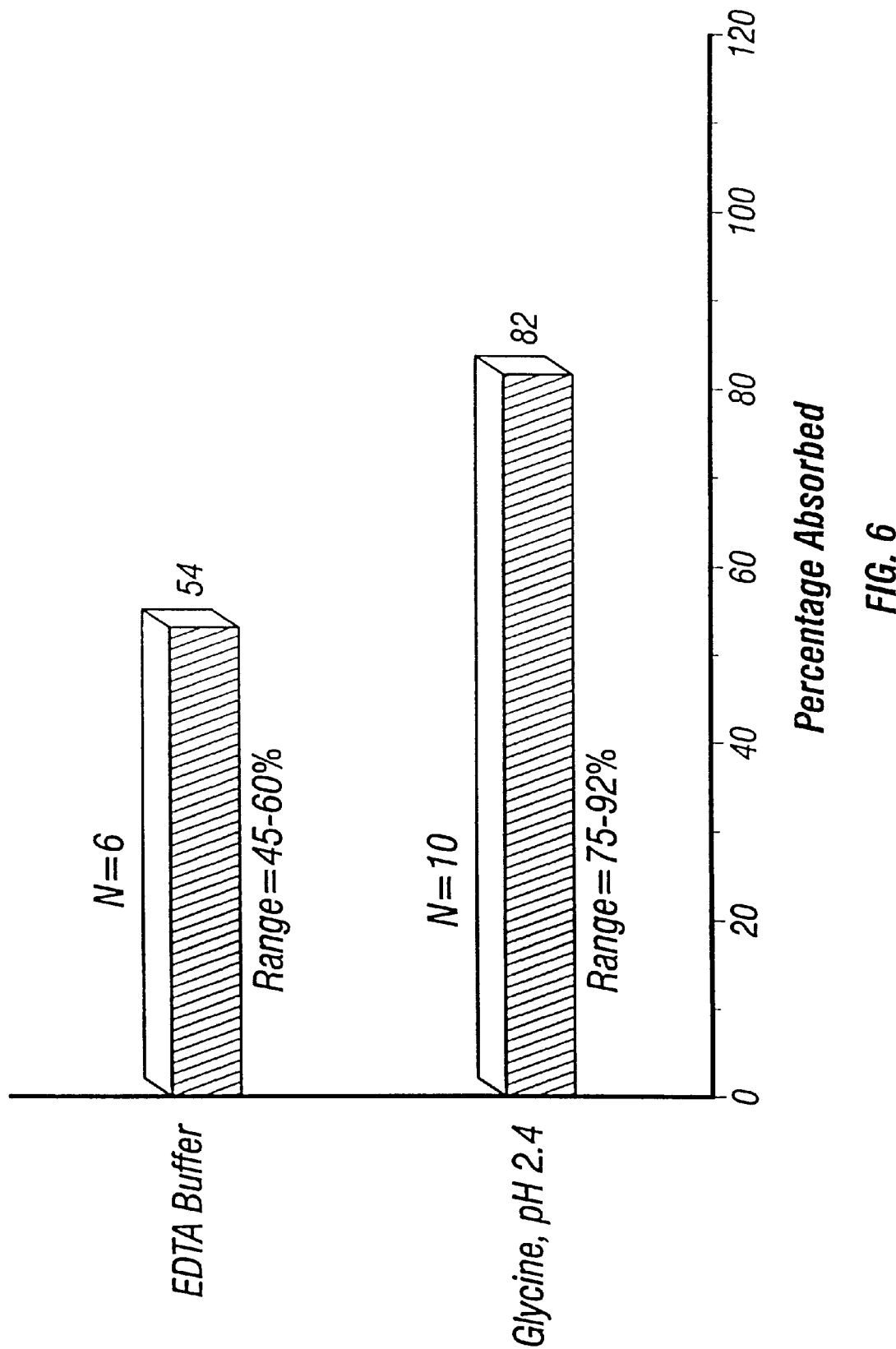

FIG. 6. Results of six studies adsorbing $Rh_{RABBIT}$ antigen to HIC beads at neutral pH in EDTA buffer and 10 separate studies adsorbing in 0.2 M Glycine, pH 2.4. Absorption and $OD_{280}$ determinations were done as in FIG. 4.

Figure 7:
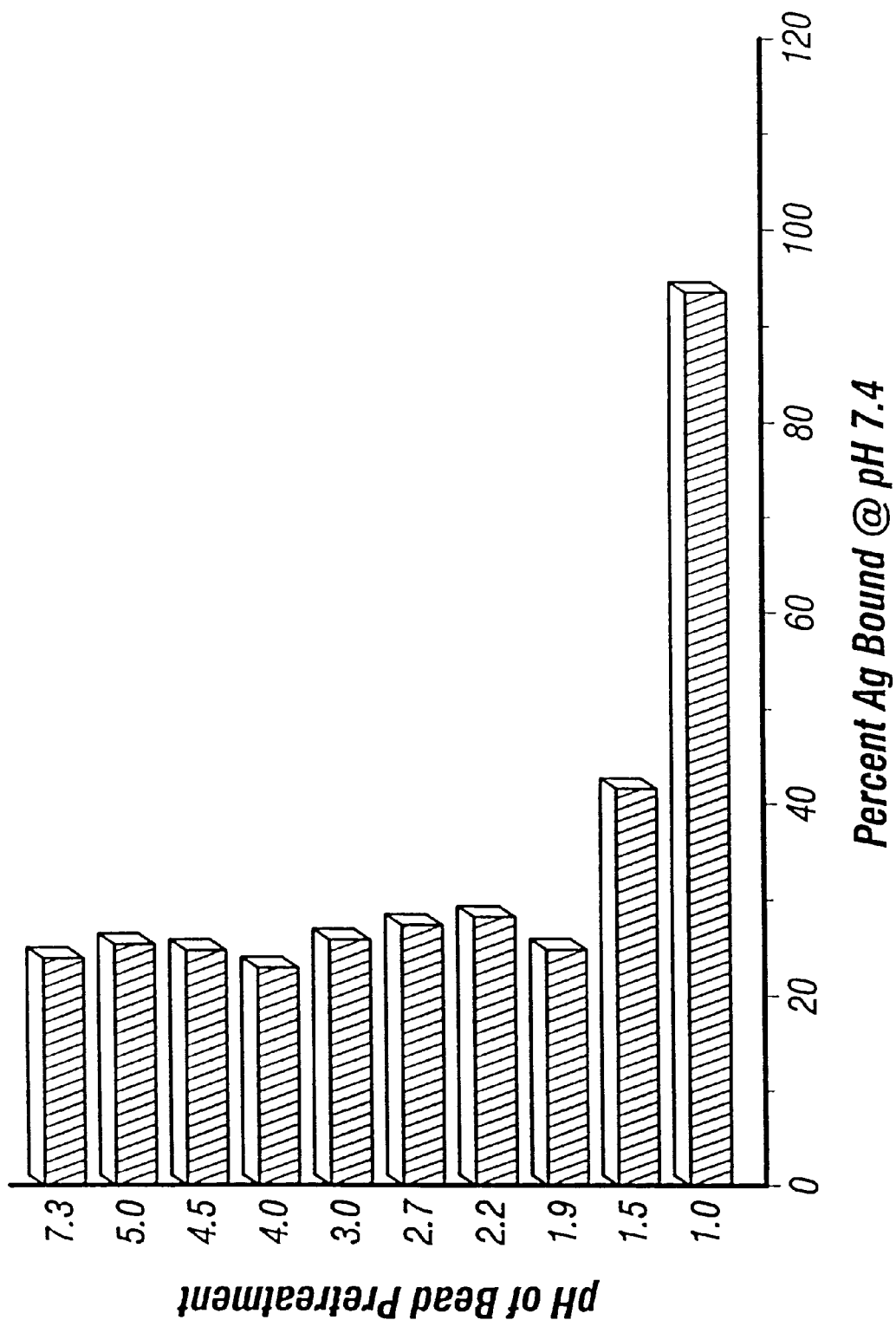

FIG. 7. HIC beads were incubated in Glycine buffers ranging from pH 1.0 to 7.3 over-night with agitation, and washed in EDTA Buffer, pH 7.4 until the pH of each set was at 7.4. $Rh_{RABBIT}$ antigen in EDTA Buffer, pH 7.4 was added and the mixtures were agitated overnight. The sets of beads were then centrifuged and washed 3 times. Each set of supernatants from each bead set was measured for volume and $OD_{280}$ and the total percentage of antigen adsorbed to bead sets was determined by subtraction.

Figure 8:
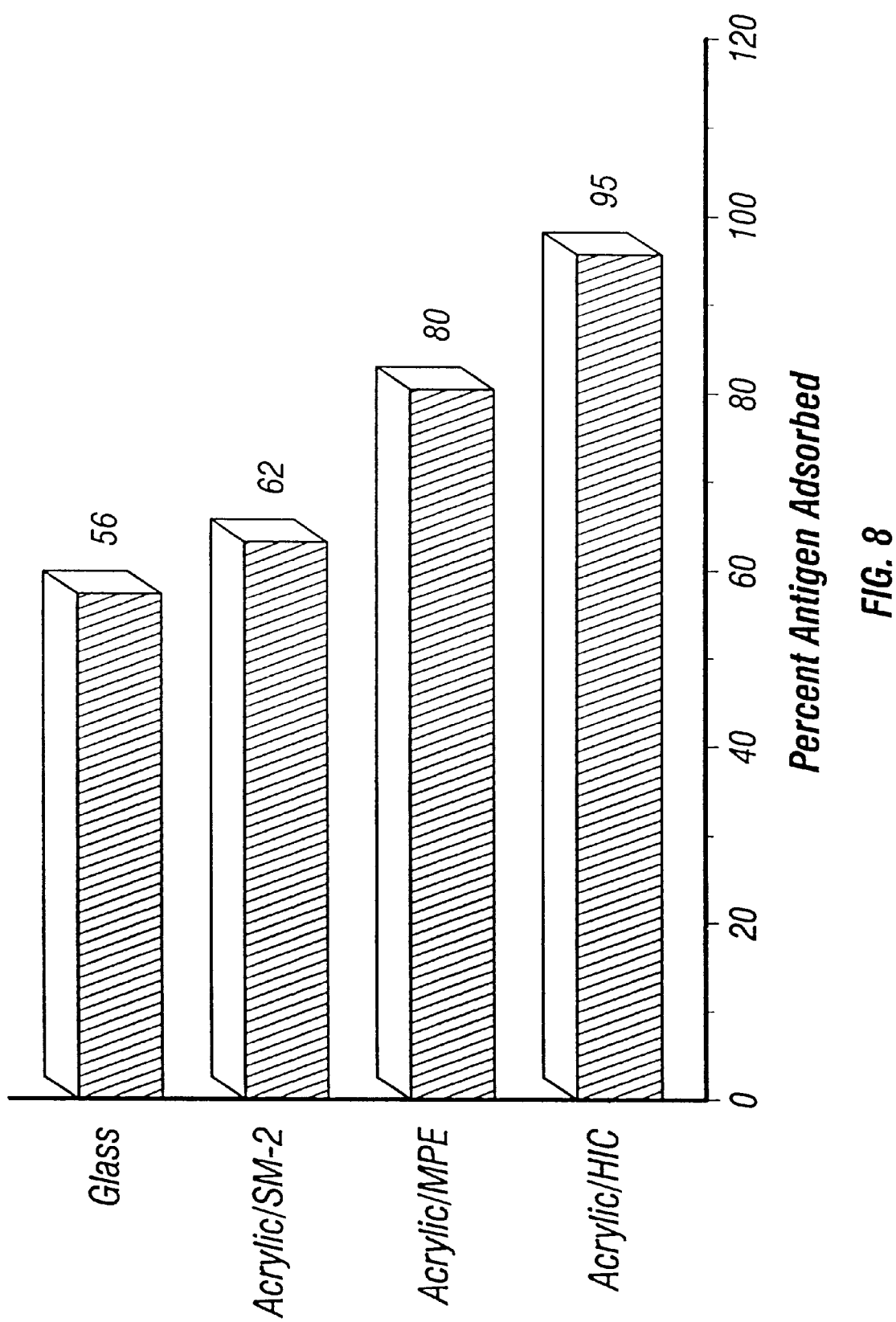

FIG. 8. Three types of plastic beads and glass beads were coated with rabbit Rh antigen in glycine buffer at pH 2.4 as described in FIG. 4. All bead types were approximately 50 μm diameter. Following centrifugation and supernatant analysis the percentage of Rh antigen adsorbed to beads was determined by subtraction.

Figure 9:
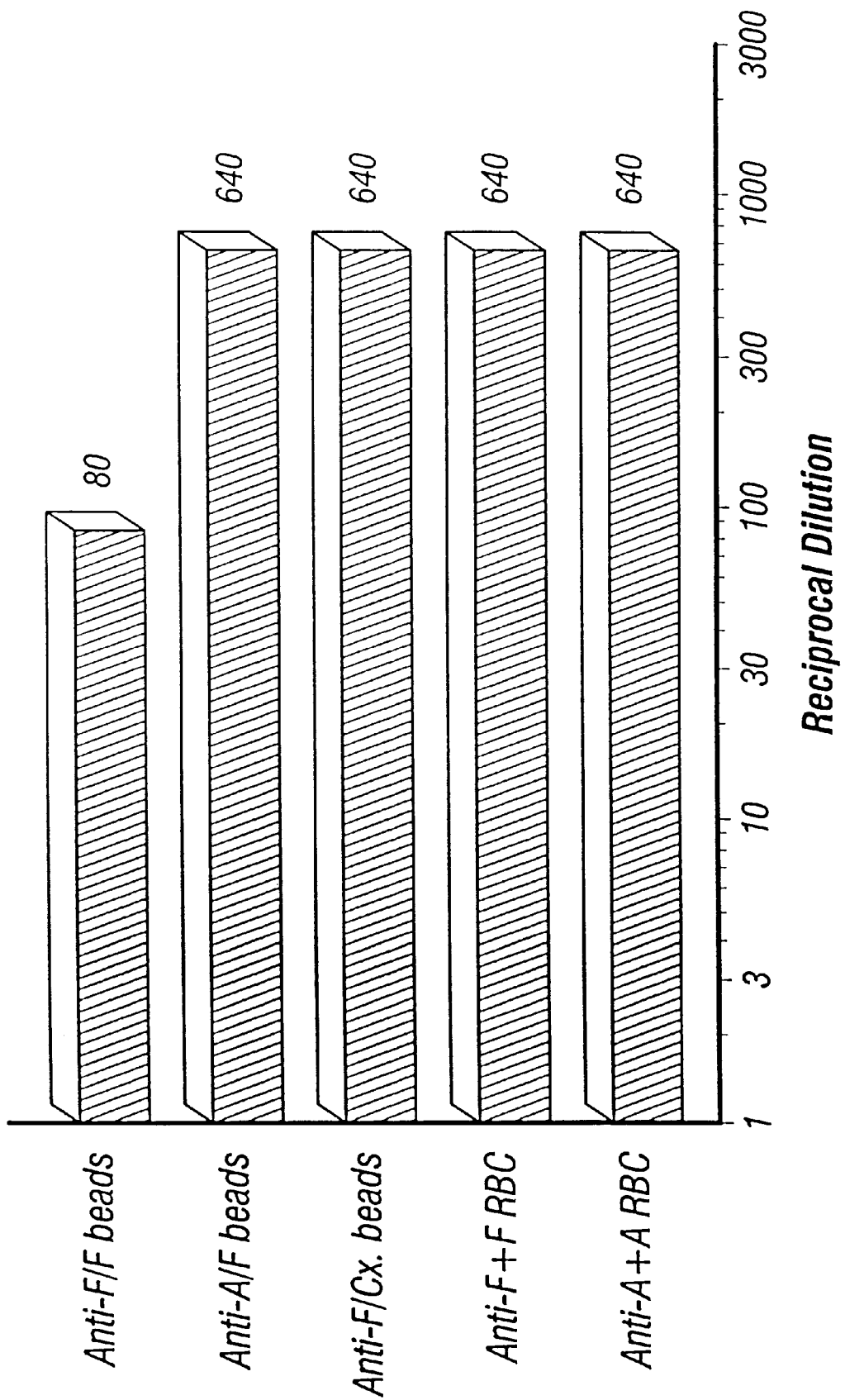

FIG. 9. Bio-Rad t-butyl HIC beads were coated with $Rh_{RABBIT}$ F antigen. One aliquot of naked (uncoated) beads and 2 aliquots of $Rh_{RABBIT}$ F-coated beads were prepared. An aliquot of each antisenun (anti-$Rh_{RABBIT}$ A and anti-$Rh_{RABBIT}$ F) was prepared to give an agglutination titer of 1:640 with homologous RBC. Aliquots of anti-$Rh_{RABBIT}$ F were mixed with either control beads (Cx. beads) or $Rh_{RABBIT}$ F-coated beads. An aliquot of anti-$Rh_{RABBIT}$ A was also mixed with $Rh_{RABBIT}$ F-coated beads. The resulting supernatants were assayed by slide agglutination assays.

Figure 10:
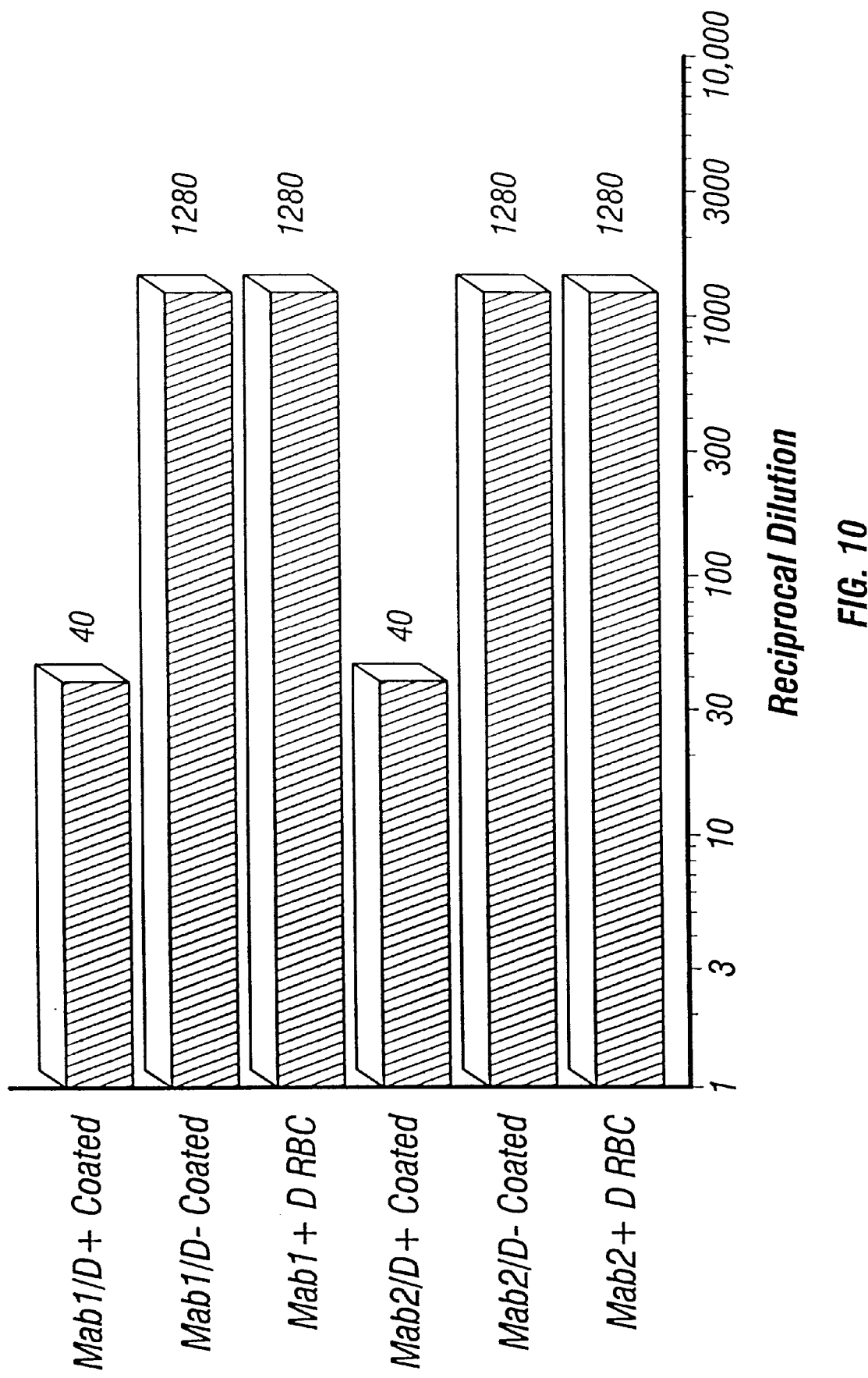

FIG. 10. Antigen extracts from both D⁺ and D⁻ RBCs were prepared. Each extract was then coated on t-Butyl HIC beads at pH 2.4 in Glycine buffer. Two monoclonal anti-D antibodies were absorbed with either D⁺ antigen-coated beads or D⁻ antigen-coated beads. Supernatants were then examined in slide agglutination assays with Ficin treated D⁺ RBCs.

Figure 11:
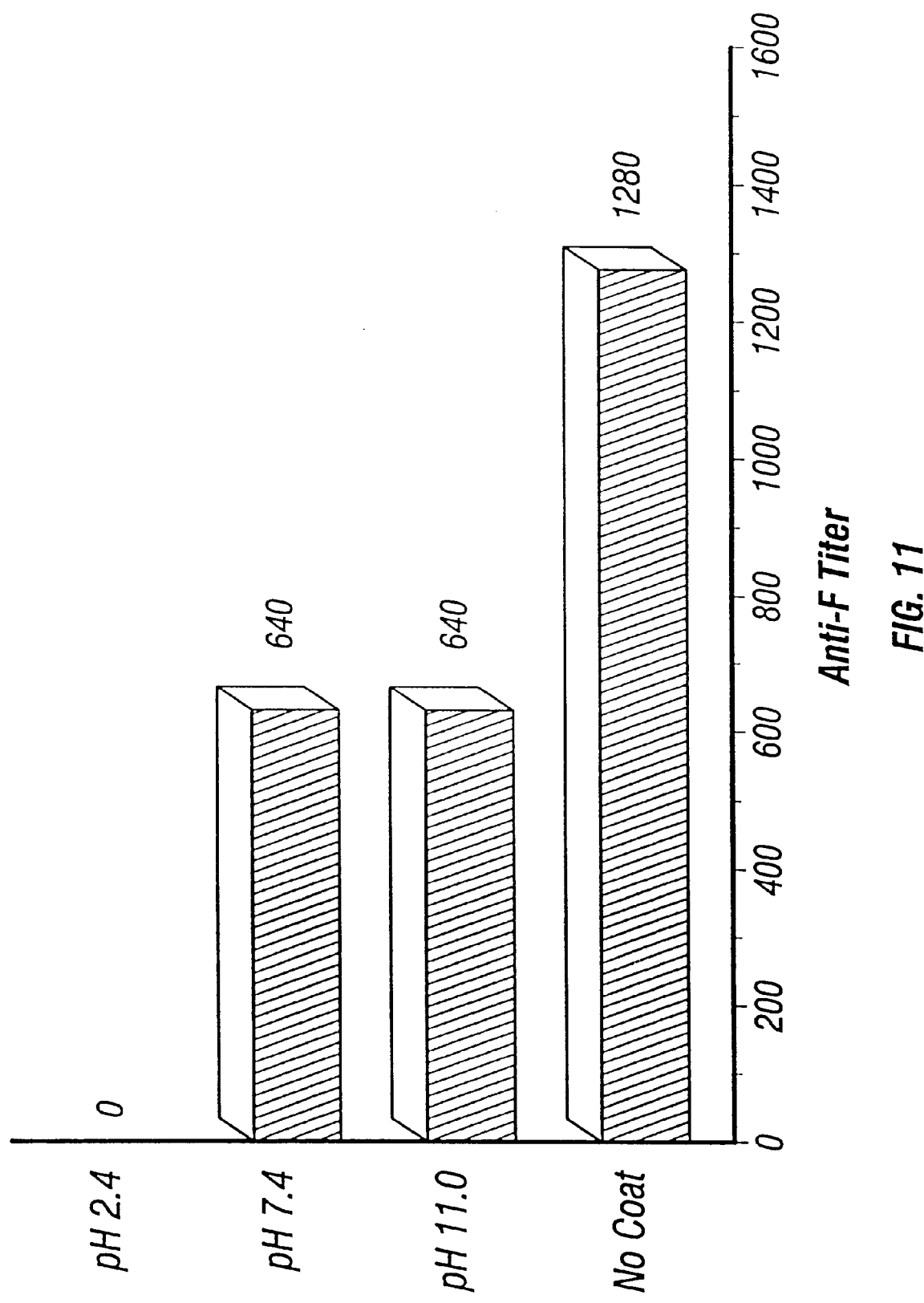

FIG. 11. Bio-Rad t-Butyl HIC beads were coated with rabbit F antigen at pH 2.4, 7.4 and 11.0 and washed. Control beads (No Coat) were also used. Anti-F serum was diluted to give a titer of 1:1,280 after absorption with naked beads (bottom bar in FIG. 11). After absorption of identical aliquots of anti-F with beads coated at pH 2.4, 7.4 and 11.0, the supernatants were assayed by slide agglutination assays using trypsin treated rabbit F RBC.

Figure 12:
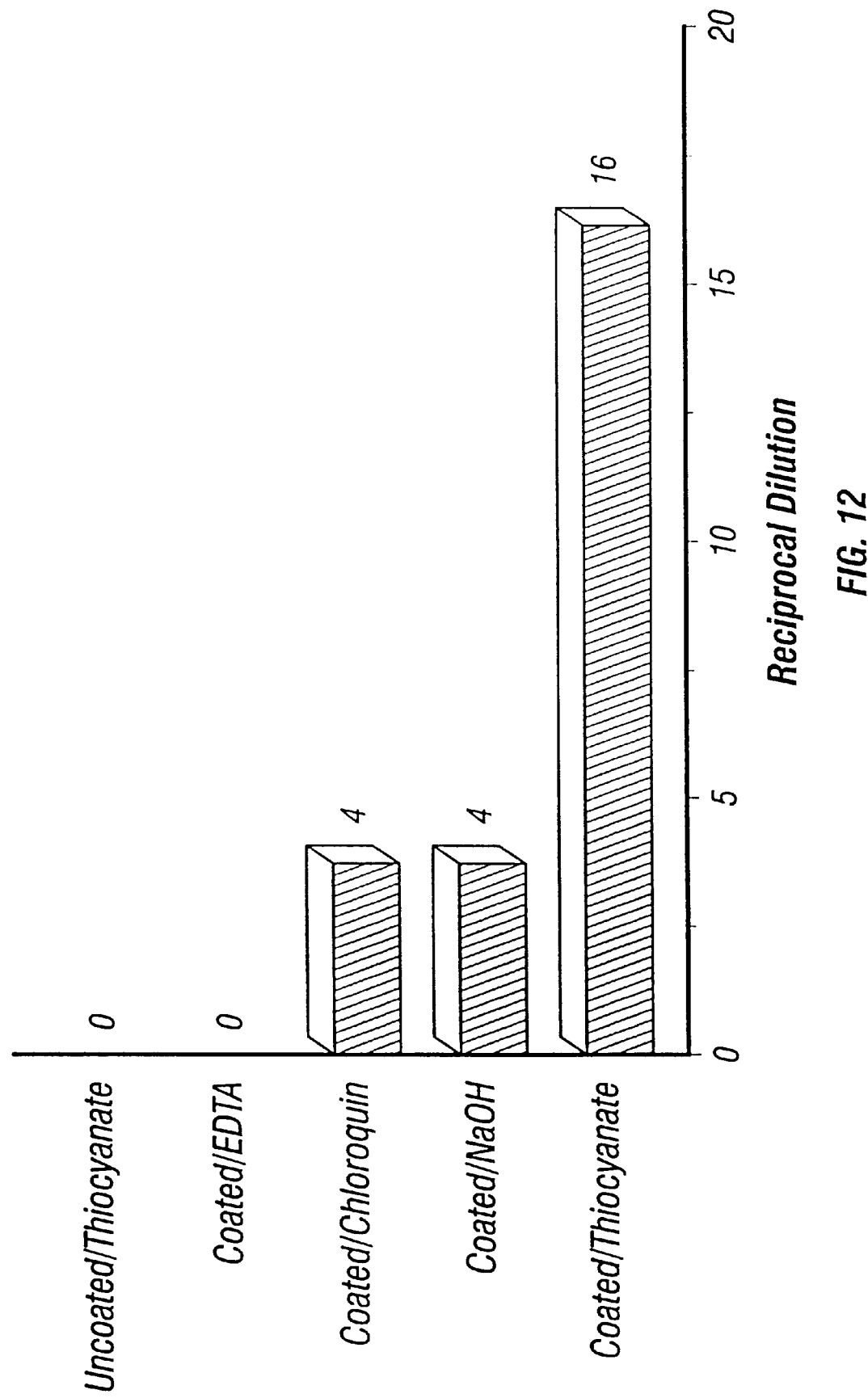

FIG. 12. Bio-Rad t-Butyl HIC beads were coated with rabbit F antigen. Aliquots of beads were then mixed with anti-F antiserum, washed, and treated with three eluting agents (3 M $NH_4$ thiocyanate, pH 4.5; 200 mg/ml chloroquin diphosphate; NaOH solution at pH 11.5). Supernatants were exhaustively dialyzed against PBS and each supernatant was then titrated using trypsinized F RBC in a slide agglutination assay.

Figure 13:
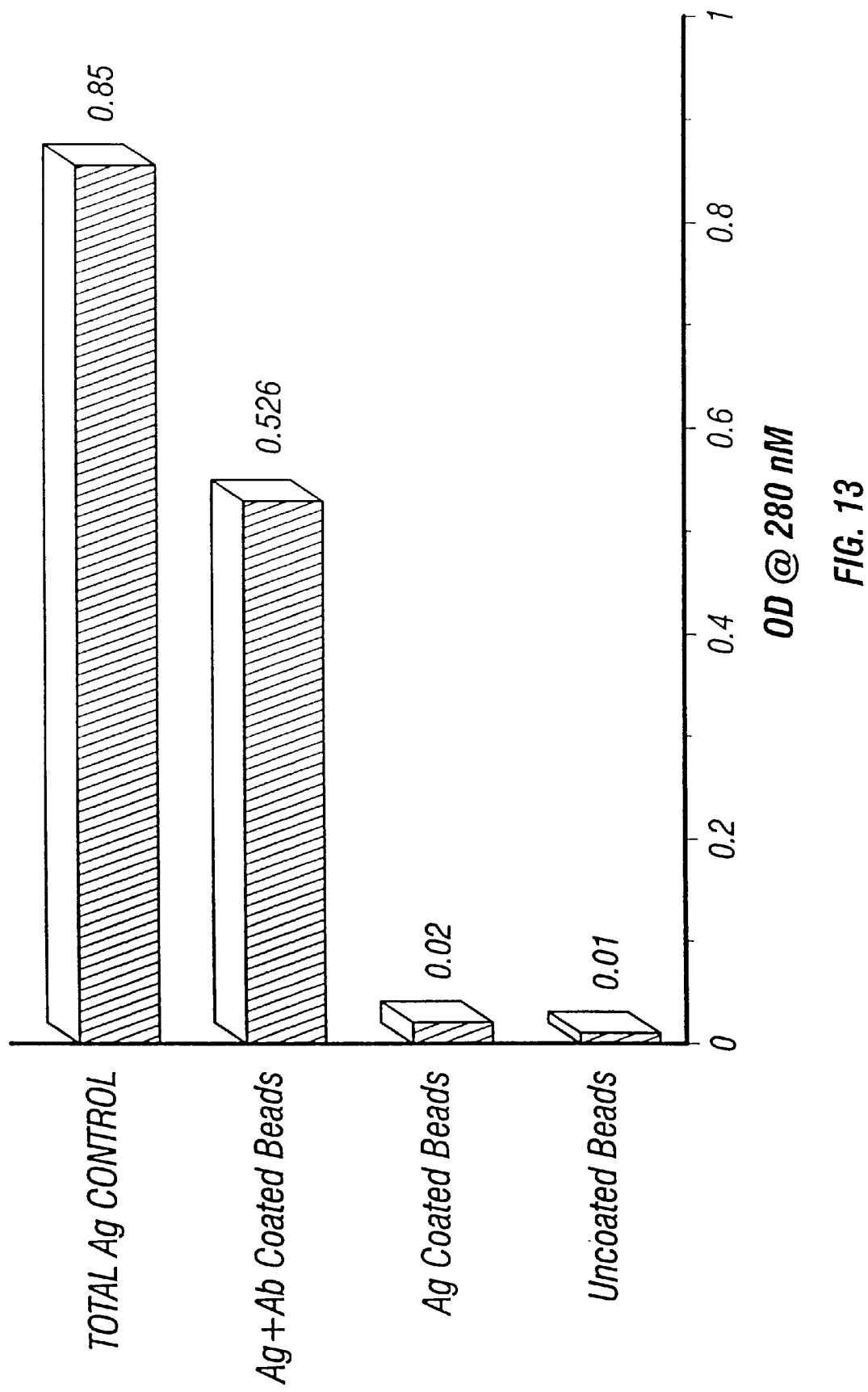

FIG. 13. Bio-Rad t-Butyl HIC beads were coated with rabbit F antigen. It was determined that aliquots of beads had adsorbed a total of 0.85 $OD_{280}$ units of Rh antigen (top bar). The supernatant of an aliquot of beads which had been mixed with anti-F anti-bodies and eluted with 3 M thiocyanate had an $OD_{280}$ of 0.526 following dialysis in PBS (second bar from top) and beads coated only with $Rh_{RABBIT}$ F antigen (no anti-F added) and naked bead supernatants had negligible $OD_{280}$ after dialysis (bars 3 and 4 from top).

Figure 14:
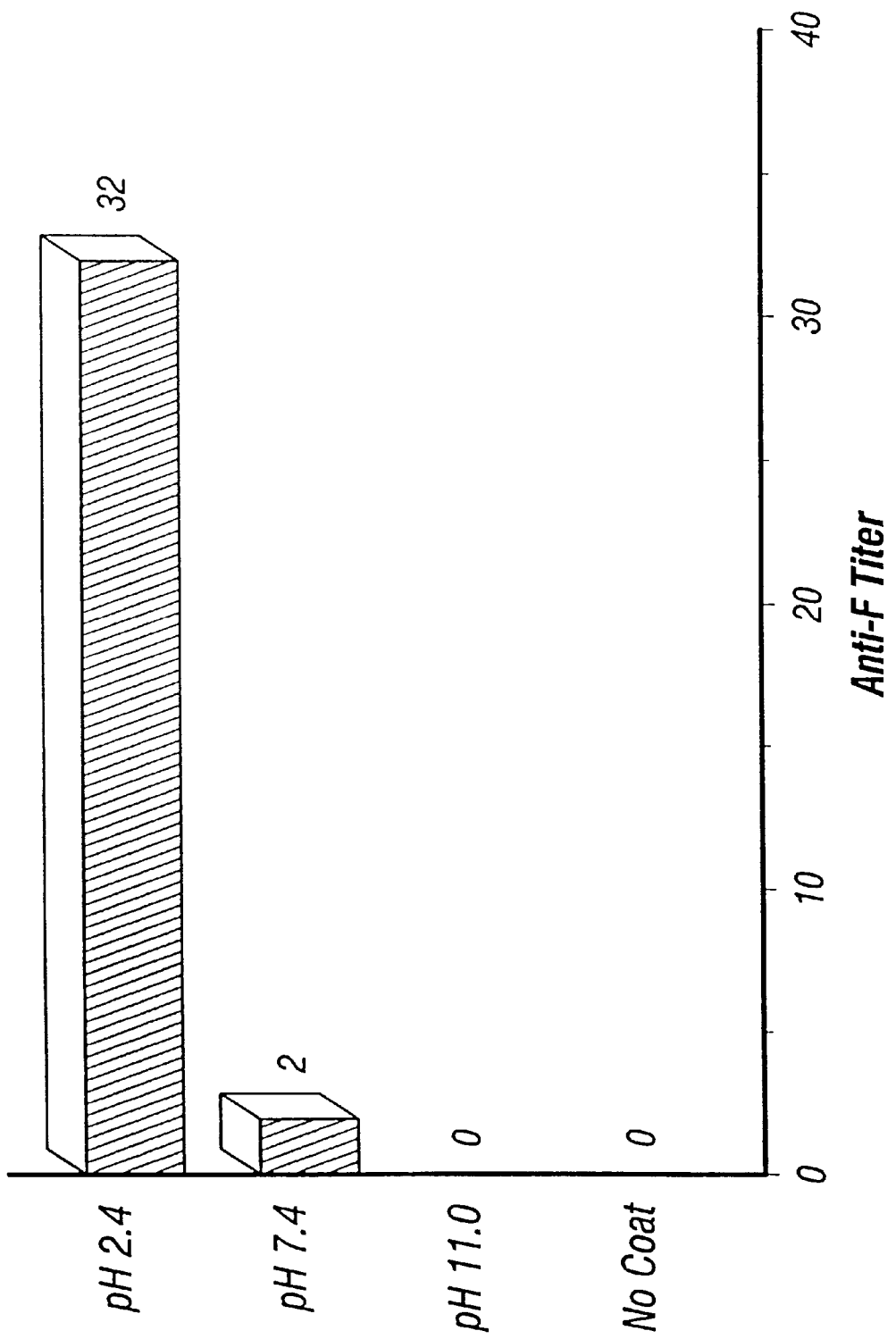

FIG. 14. Antibody titers of 3 M thiocyanate eluates from aliquots of Bio-Rad t-Butyl HIC beads in FIG. 11 following exhaustive dialysis vs. PBS. Titers were determined using trypsinized $Rh_{RABBIT}$ F RBC in a slide agglutination assay.

Figure 15:
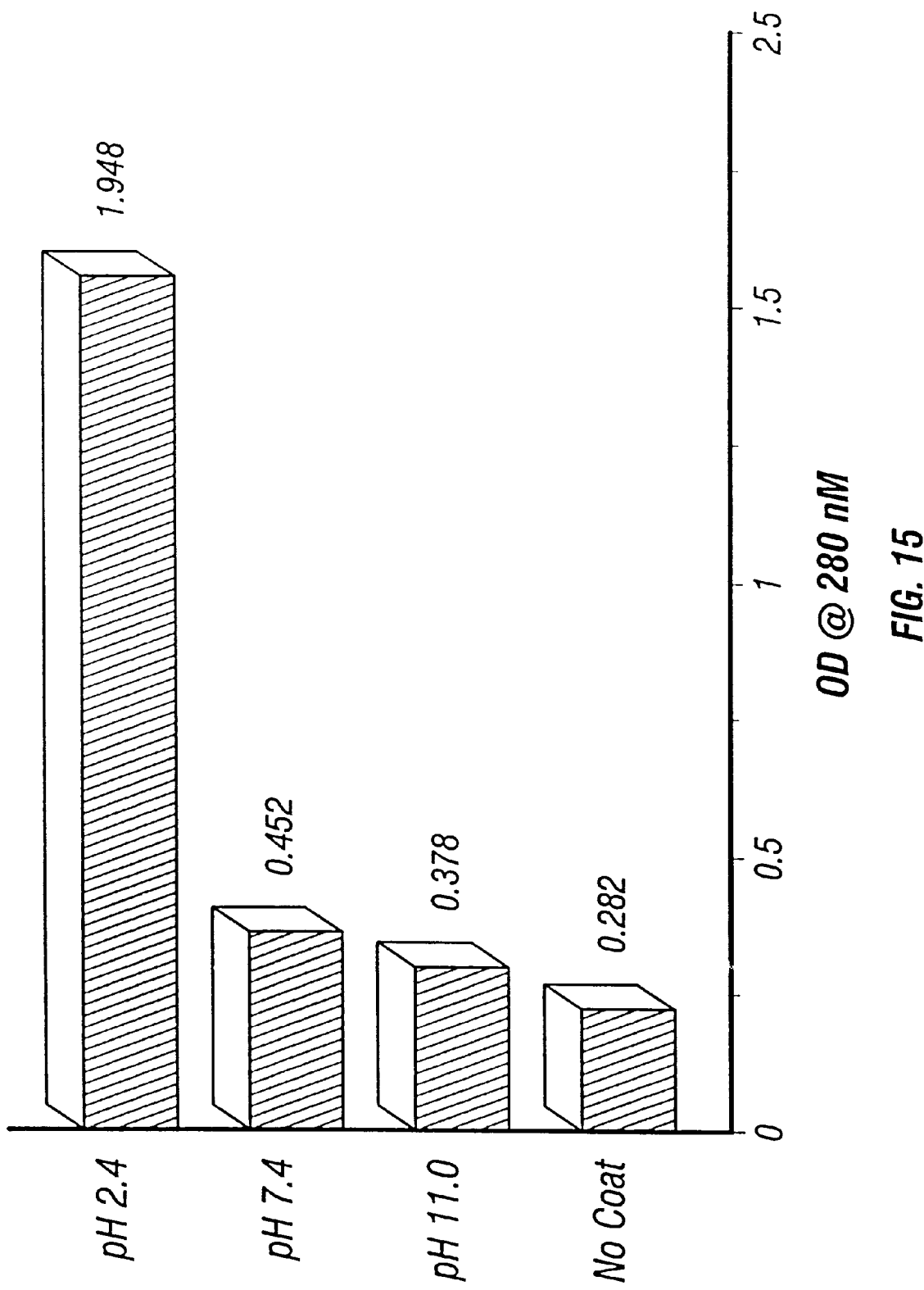

FIG. 15. Optical density of eluates from FIG. 11. After dialysis vs. PBS determined spectrophotometrically.

Figure 16:
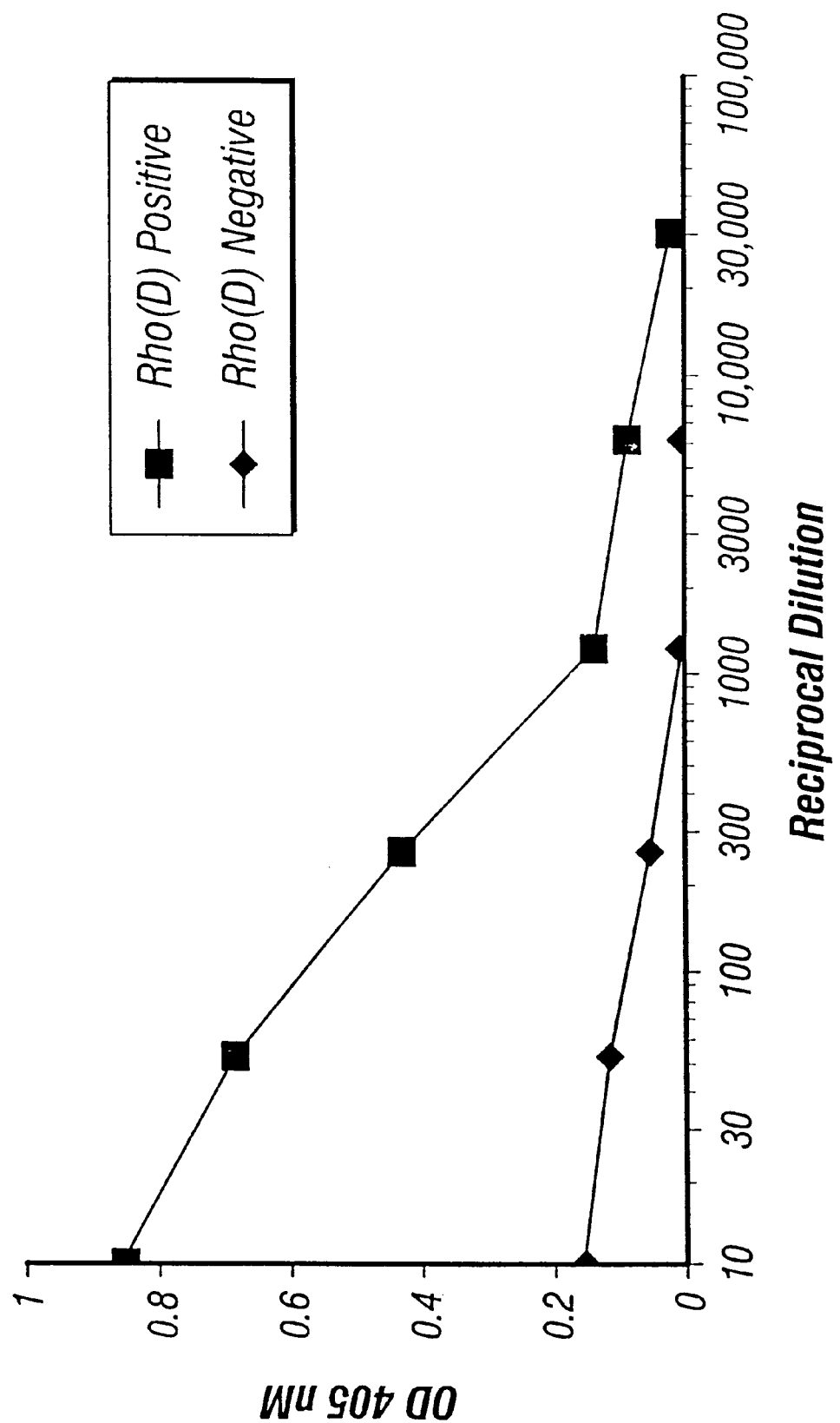

FIG. 16. Enzyme linked immunoadsorbent assay using polystyrene plates coated with either $Rh^+$ or $Rh^-$ antigen extracts in 0.2 M glycine buffer, pH 2.4. Monoclonal human anti-D was used as test antibody.

Figure 17:
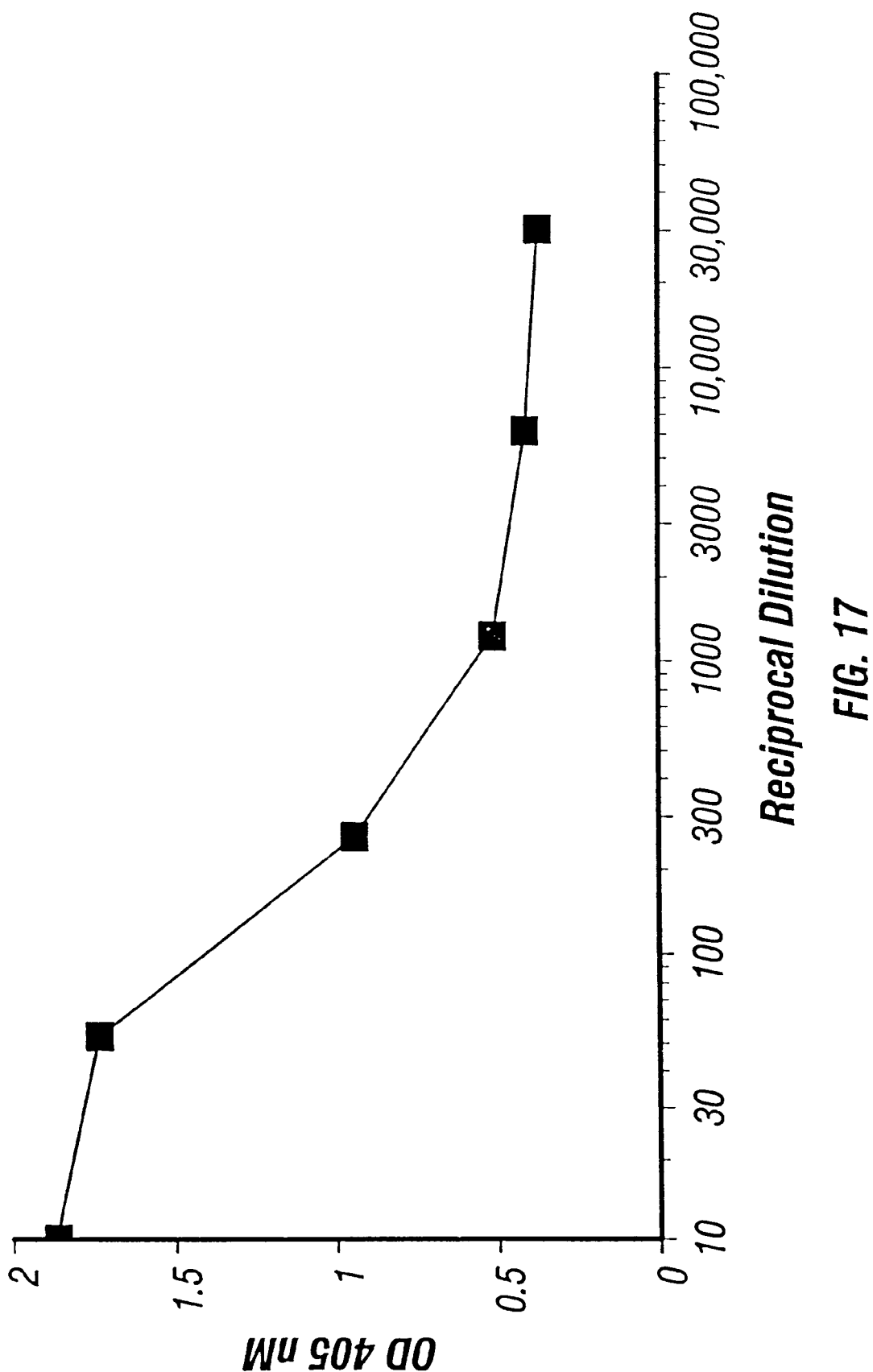

FIG. 17. Enzyme linked immunoadsorbent assay using polystyrene plates coated with rabbit F antigen in 0.2 M Glycine buffer, pH 2.4. Rabbit allo-anti-F was used as test antibody.

FIG. 18. Schematic diagram showing the apparatus and methods of the present invention used for the removal of blood group-specific antibodies from solution. In a preferred embodiment, the methods and devices are used for the inline removal of Rh antigens from solution. A solution suspected of containing Rh antibodies (in this case, a circulatory system of an animal) is passed over the column and the Rh antibodies are bound to the column and removed from the circulating fluid.

FIG. 19A. Side view of an example of the apparatus of the invention for the removal of antibodies from solution. The apparatus comprises a chamber with one or more inlet and one or more outlet ports through which the solution is passed. Within the chamber is a matrix to which one of the disclosed serologically-active blood group antigens is adsorbed. This schematic illustrates a device which is contemplated by the inventors for use in the removal of specific blood group antibodies from solution using the serologically-active antigen-bound matrices of the present invention. In one embodiment, the device is used to purify antibodies which bind to the matrix. This may be done by washing the column after binding to elute contaminating substanecs, and then the substantially-purified antibodies may be eluted from the device using an appropriate eluant.

FIG. 19B. Cross-sectional view of an example of the apparatus of the present invention. Shown is a chamber having an inlet and an outlet port, and a matrix within the chamber to which is adsorbed the novel antigenically-active blood group antigens of the invention. The apparatus may optionally further comprise one or more pumps for supplying a sample to the matrix for the removal of anti-blood group antibodies. The matrix may contain one or more blood group antigens as disclosed.

4. DESCRIPTION OF ILLUSTRATIVE EMBODIMENTS 4.1 Some Advantages of the Invention Those of ordinary skill having the benefit of this disclosure will appreciate that the invention provides a number of advantages, including the following:

4.1.1 Isolation and Quantitation of Antigenically-Active Blood Group Antigens

The present invention provides new and important methods of isolating, preparing storing, and quantitating antigenically-active blood group antigens, proteins, and peptides derived therefrom, and in particular, Rh antigens such as the $Rh_o$ D antigen. Also provided are novel methods of identifying, quantitating, and removing anti-blood group antibodies, and in particular, anti-Rh antibodies from solution. In a most preferred embodiment, anti-$Rh_o$ D antibodies are identified, quantitated and removed from solution using the novel antigens described herein.

4.1.2 Availability of Solid-Phase Blood Group Antigens

The present invention provides the first successful adsorption of serologically active blood group antigens, and in particular, active Rh antigens such as D antigen to a solid support or substrate, and in particular plastic beads and ELISA plates. Surprisingly, the inventors have shown that more of the antigen is adsorbed/bead at low pH than when the adsorption is done with the antigen in a neutral extraction buffer. These results were quite surprising and unexpected for the blood group antigen peptides, since it is well-known in the art that most proteins are denatured in low pH solutions, and that most peptide antigens are antigenically inactive (serologically-inactive) below neutral pH conditions. That the inventors have demonstrated Rh antigen activity in a pH range of from about 6 to about 1, and most preferably at a pH of from about 2.4 to about 4.5 represents a breakthrough in the preparation of solid-phase RBC antigens, and solid-phase Rh antigens in particular.

4.1.3 Isolation of anti-Rh Antibodies from Solution

The inventors have also demonstrated that Rh antigen bound under conditions of low pH absorbs more antibody/jig of antigen extract solution than when the antigen is adsorbed at standard neutral pH. Moreover, chaotropic reagents (e.g., 3 M $NH_4SCN$) can successfully elute bound antibodies from antigen-coated solid supports or substrates.

The present invention also encompasses methods for using the compositions disclosed herein in highly efficient techniques for the in vitro and ex vivo isolation and purification of anti-Rh IgG antibodies. The methods and compositions of the invention can be used to produce high yields of Rh-specific antibodies. In preferred embodiments, Rho D antigen compositions are used to isolate and purify anti-$Rh_o$ D antibodies from solution. Such methods are most useful in the area of treating HDN, and in the removal of anti-Rh antibodies from the bloodstream of a pregnant female.

4.1.4 Active Rh Antigen Provides Alternatives to Treatment of HDN

Liley (1963) introduced the method of intraperitoneal intrauterine transfusion for the human fetus affected by severe alloimmune Rh antibodies. In utero therapy has now advanced to the point of using ultrasound guided umbilical vessel puncture with direct i transfusion of RBC to the anemic fetus (Bang et al., 1982). Despite this therapy, fetal mortality rates of 10–25% continue to be reported (Grannum et al., 1986; Berkowitz et al., 1986).

The availability of devices and methods for the removal of antibodies from the bloodstream of a pregnant female obviates the need for such transfusion methods and greatly reduces the likelihood of HDN. By reducing the titer of Rh antibodies in the bloodstream through absorption to active immobilized Rh antigen compositions disclosed herein, the concentration of anti-Rh antibodies may be significantly reduced in the mother. In a conventional scenario where intrauterine transfusion is used to reduce the anti-Rh titer, typically 6 or more transfusions are performed with such procedures costing in excess of $50,000. The inventors contemplate the inline reduction of Rh antibodies from the mother's circulatory system using the devices and compositions disclosed herein to be substantially less expensive with an estimated fetal saving of 10–15%.

4.1.5 Methods and Compositions Provide Rabbit A, D, and F RBC Antigens

It is clear that the rabbit A, D and F blood group antigens are phylo-genetically equivalent to the human Rh blood group antigen system, and therefore, the present invention also provides methods and compositions for rabbit RBC antigen isolation, purification, as well as identification and quantitation of rabbit RBC antigens and antibodies in solution. Kellner and Hedal (1953) showed that the antigens were restricted to the RBC and that there was no detectable secretion of them into any body fluids, similar to the human Rh antigen. Additionally, Cohen (1982) pointed out that, due to the complexity of these antigens and their ability in the heterozygous state to create complex antigens, that they must be polypeptides rather than simple sugar residues placed in strategic terminal positions by a gene-controlled transferase. The compound antigens created by different combinations of A, D, or F antigens have been studied extensively in the rabbit (Cohen, 1982; Cohen and Tissot, 1974) and compound antigens derived from combinations of different Rh antigens have been described for the human (Zaleski et al., 1983) as well. Further, the A, D, and F antigens in rabbits can mediate HDN (Anderson, 1956) as does the Rh antigen in humans.

4.2 "Carter Rh Antigen" Preparations Are Actually Devoid of Antigen

In early papers by Carter and coworkers, methods were described for isolating the "Rh hapten" from red blood cells. Unfortunately, the work is now generally considered invalid, as scientists have been unable to identify or purify Rh antigen using the disclosed methods. In fact, the present inventors were unable to isolate Rh antigen using any of the methods in the prior art as taught by Carter and coworkers. Nine separate attempts were made to repeat the Carter work. The inventors used the exact method of extraction as described in the early literature: five times with ether and four times with dichloromethane. All extracts obtained had the color and physical properties consistent with the published reports, but all such preparations were uniformly devoid of Rh antigen. No activity was seen even when the inventors performed the inhibition assays described in the Carter protocols (Carter, 1949). In no case was any inhibition seen. Therefore, previously reported methods proved unreliable in isolating soluble active Rh antigen.

4.3 Therapeutic and Diagnostic Kits Comprising Rh Antigen Compositions

Therapeutic kits comprising, in suitable container means, an Rh antigen composition of the present invention in a pharmaceutically acceptable formulation represent another aspect of the invention. The Rh composition may be native Rh antigen, truncated Rh antigen, site-specifically mutated Rh antigen, or Rh antigen-encoding peptide epitopes, or alternatively antibodies which bind native Rh antigen, truncated Rh antigen, site-specifically mutated Rh antigen, or Rh antigen -encoded peptide epitopes. In other embodiments, the Rh antigen composition may be nucleic acid segments encoding native Rh antigen polypeptides, truncated Rh antigen polypeptides, site-specifically mutated Rh antigen polypeptides, or Rh antigen-encoding peptide epitopes. Such nucleic acid segments may be DNA or RNA, and may be either native, recombinant, or mutagenized nucleic acid segments.

The kits may comprise a single container means that contains the Rh antigen composition. The container means may, if desired, contain a pharmaceutically acceptable sterile excipient, having associated with it, the Rh antigen composition and, optionally, a detectable label or imaging agent. The single container means may contain a dry, or lyophilized, mixture of an Rh antigen composition, which may or may not require pre-wetting before use.

Alternatively, the kits of the invention may comprise distinct container means for each component. In such cases, one container would contain the Rh composition, either as a sterile polypeptide antigen or polypeptide antibody solution or in a lyophilized form, and the other container would include the solid matrix, which may or may not itself be pre-wetted with a sterile solution, or be in a gelatinous, liquid or other syringeable form.

The kits may also comprise a second or third container means for containing a sterile, pharmaceutically acceptable buffer, diluent or solvent. The presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The matrix may also be aliquotted into smaller containers, should this be desired. The kits of the present invention may also include a means for containing the individual containers in close confinement for commercial sale, such as, e.g., injection or blow-molded plastic containers into which the desired vials, columns, microtiter plates, particulate fiber, or glass wool matrices, affinity columns, inline adsorption devices, syringes, tubes, or other containers are retained.

Irrespective of the number of containers, the kits of the invention may also comprise, or be packaged with, a device for in-line or ex vivo placement of the antigen-matrix composition for use in treatment of an animal. Such an instrument may be a syringe, pipette, column, filtration resin or similar matrix, or any such medically approved in-line solid-phase antigen containing antibody purification device.

4.4 Affinity Chromatography

Affinity chromatography is generally based on the recognition of a protein by a substance such as a ligand or an antibody. The column material may be synthesized by covalently coupling a binding molecule, such as an antigenic protein, for example an Rh protein, to an insoluble matrix such as Teflon™, styrene, glass, plastic, cellulose, polyester, polystyrene, etc. The column material is then allowed to absorb the desired substance from solution. Next, the conditions are changed to those under which binding does not occur and the substrate is eluted. The requirements for successful affinity chromatography are:

1) that the matrix must specifically-absorb the molecules of interest;
2) that other contaminants remain unabsorbed;
3) that the ligand must be coupled without altering its binding activity;
4) that the ligand must bind sufficiently tight to the matrix; and 5) that it must be possible to elute the molecules of interest without destroying them, or eluting the ligand.

A preferred embodiment of the present invention is an affinity chromatography method for purification of antibodies from solution wherein the matrix contains adsorbed Rh antigen compositions or peptide epitopes derived from one or more Rh antigen polypeptides, adsorbed to a solid-phase matrix such as Sepharose, Teflon™, nylon, plastic, glass, or other suitable matrix. Suitable types of Sepharose matrices include CL6B, CL4B, and related resins which are known to those of skill in the art. This antigen-matrix binds the antibodies of the present invention directly and allows their separation by elution with an appropriate reagent such as a chaotropic reagent (e.g., $NH_4SCN$, NaSCN, KSCN, etc.) Another preferred embodiment of the present invention is an affinity chromatography method for the purification of Rh antigen polypeptides and peptide epitopes from solution. The matrix may include covalently coupled anti-Rh antibodies specifically reactive for the Rh antigen polypeptides. Means for the coupling of antibodies to solid-phase matrices are well-known to those of skill in the art. The antibody-matrix facilitates the isolation and separation of Rh antigen polypeptides from solution by elution with a suitable buffer as described above.

4.5 Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of Rh antigen-derived proteins and peptides is not limited to such assays, and that other useful embodiments include RIAs and other non-enzyme linked antibody binding assays and procedures.

In preferred ELISA assays, proteins or peptides incorporating Rh antigens, rRh antigens (recombinant Rh antigens), or Rh antigen-derived amino acid sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antiserum, such as bovine serum albumin (BSA) or casein, onto the well. This allows for blocking of nonspecific adsorption sites on the immobilizing surface and thus reduces the background caused by nonspecific binding of antiserum onto the surface.

After binding of antigenic material to the well, coating with a non-reactive material to reduce background, and washing to remove unbound material, the immobilizing surface is contacted with the antiserum or clinical or biological extract to be tested in a manner conducive to immune complex (antigen/antibody) formation. Such conditions preferably include diluting the antiserum with diluents such as WRA, glycine, (or other amphoteric buffer), BSA, bovine gamma globulin (BGG), or short-term exposure to phosphate buffered saline (PBS)/Tween™. These added agents also tend to assist in the reduction of nonspecific background. The layered antiserum is then allowed to incubate for, e.g., from 2 to 4 hours, at temperatures preferably on the order of about 4° to about 37° C. Following incubation, the antisera-contacted surface is washed so as to remove non-immunocomplexed material. A preferred washing procedure includes washing with a amphoteric or zwitterionic buffer solution such as WRA, glycine, or alternatively, for short-term exposure to the buffer, PBS, PBS-Tween®, or borate solutions are acceptable.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in an amphoteric buffer such as WRA, glycine, or the like, or alternatively, for a short time in a standard buffer such as PBS or PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

4.6 Immunoprecipitation

The anti-Rh antibodies of the present invention are particularly useful for the isolation of Rh antigens by immunoprecipitation. Immunoprecipitation involves the separation of the target antigen component from a complex mixture, and is used to discriminate or isolate minute amounts of protein. For the isolation of cell-surface localized proteins such as Rh antigen polypeptides, peptides may be solubilized from the RBC membrane using methods that are well-known to those of skill in the art. General methods of peptide isolation involve dissolving cells in one of several detergents, such as Triton X-100™ or alternatively, dissolving membrane skeletons in SDS, and subsequently purifying the Rh polypeptides from solution either by hydroxylapatite chromatography and/or preparative electrophoresis (Agre et al., 1987).

4.7 Western Blots

The compositions of the present invention will find great use in immunoblot or Western blot analysis. The anti-Rh antibodies may be used as high-affinity primary reagents for the identification of proteins immobilized onto a solid support matrix, such as nitrocellulose, nylon or combinations thereof In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods in conjunction with Western blotting (including enzymatically-, radiolabel-, or fluorescently-tagged secondary antibodies against the toxin moiety) are considered to be of particular use in this regard.

4.8 Pharmaceutical Compositions

In methods involving the administration of antigens or antibodies to an animal, it is necessary to provide pharmaceutically-acceptable preparations of such compositions. Likewise, the use of in-line medical devices for isolation of anti-Rh antibodies also requires the use of appropriate medically-acceptable formulations of the compositions disclosed herein. In this respect, several classes of pharmaceutical preparations may be contemplated. For example, the compositions may be orally administered with an inert diluent or with an assimilable edible carrier, or they may be enclosed in hard or soft shell gelatin capsule, or they may be compressed into tablets, or they may be incorporated directly with the food of the diet. The compositions may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may alternatively, be administered intravenously, parenterally or intraperitoneally. Solutions of the active compounds as free base or pharmacologically-acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically-active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.9. Epitopic Core Sequences

It is proposed that particular advantages of the present invention may be realized through the preparation of synthetic blood group antigen proteins or peptides which include modified and/or extended epitopic/immunogenic core sequences which result in a "universal" epitopic peptide directed to Rh antigen and Rh antigen-related sequences, or other domains which bind anti-Rh antibodies. It is proposed that these regions represent those which are most likely to promote T-cell or B-cell stimulation in an animal, and, hence, elicit specific antibody production in such an animal.

To confirm that a protein or peptide is immunologically cross-reactive with, or a biological functional equivalent of, one or more epitopes of the disclosed peptides is also a straightforward matter. This can be readily determined using specific assays, e.g. of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs; Western or dot blotting and the like. In any of the competitive assays, one of the binding components, generally the known element, such as the Rh antigen -derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between an Rh antigen and any test antigen, one would first label an Rh antigen with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to an antibody of the present invention. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as an Rh antigen polypeptide, for example, will be able to effectively compete for binding to and thus will significantly reduce Rh antigen binding, as evidenced by a reduction in the amount of label detected.

The reactivity of the labeled antigen, e.g., an Rh antigen composition, in the absence of any test antigen would be the control high value. The control low value would be obtained by incubating the labeled antigen with an excess of unlabeled Rh antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (ie., consistently observed) reduction in binding.

In addition to the peptidyl compounds described herein, the inventors also contemplate that other sterically similar compounds may be formulated e.g., using recombinatorial chemical technology, to mimic the key portions of the peptide structure. Such compounds, which may be termed peptidomimetics, may be used in the same manner as the peptides of the invention and hence are also functional equivalents. These include compositions which mimic the stable active $Rh^+$ antigen complex. The generation of a structural functional equivalent may be achieved by the techniques of modeling and chemical design known to those of skill in the art. It will be understood that all such sterically similar constructs fall within the scope of the present invention.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation of Active Rh Antigen 5.1.1 Isolation of RBC Soluble Fraction

All operations were carried out at 4° C. unless noted otherwise. Lysis Buffer consisted of 0.01 M Tris-HCl, pH 7.4. Triton Buffer was made by adding Triton X-100 to a final concentration of 10% (wt/wt) in Lysis Buffer. EDTA buffer consisted of 0.1 mM EDTA (pH 8.0). Optionally, the protease inhibitor phenylmethylsulfonyl fluoride (PMSF) was added at a final concentration of 10 μg/ml, although the inventors saw no differences in results using buffer from which PMSF was omitted.

RBC were washed at least 5 times in saline. The packed RBC pellet was suspended in 20 volumes of precooled Lysis Buffer and incubated on ice for 20 min with occasional agitation. The lysate was then centrifuged at 20,000 rpm (48,000×g) in a Sorvall centrifuge using an SS-34 (8×50 ml) rotor for 15 min at 4° C. Both centrifuge and rotor were precooled to 4° C. The resulting membrane pellets were washed 4 times with 10 volumes of Lysis Buffer. The final pellet was then resuspended to the original packed RBC volume in Lysis Buffer.

One volume of the membrane suspension was made to a final 0.5% concentration of Triton-X-100® using Triton buffer and the equation given below. The solution was incubated for 15 min on ice with occasional agitation, then centrifuged for 10 min at 20,000 rpm as above. The pellet was washed at least four times with 10 volumes of Lysis Buffer to remove the residual detergent, and the last supernatant was then discarded.

The pellet was resuspended in 2 volumes of prewarmed EDTA Buffer, and incubated for 30 min at 37° C. with occasional agitation, and then centrifuged at 20,000 rpm (48,000×g) for 15 min. The pellet was then discarded and the supernatant was retained for further use. The initial volume of packed RBC above was defined as 1 volume. Thus, 10 ml of packed RBC were lysed in a total of 200 ml Lysis Buffer and the washes using 10 volumes would be 100 ml, etc.

$$0.1X=0.005(Y+X) \qquad \text{Equation 1}$$

where X is the volume of the 10% Triton Buffer solution to add and Y is the volume (in ml) of the membrane suspension used.

5.2 Example 2
Determination of Activity of Rh Antigen
5.2.1 Enzyme Treatment of Rabbit RBC Rabbit blood was collected in anticoagulant (Heparin, 20 U/ml), and centrifuged at 2,000 rpm (900×g) for 15 min at 4° C. The RBC pellet was resuspended and washed at least 3 times in normal saline (0.85% NaCl). In a tube containing 2.4 ml of PBS and 280 µl of a 1:3 dilution of Bacto Trypsin (Difco) (equivalent to 200 µg/ml trypsin) and 100 µl packed, washed RBC were added. This mixture was incubated for 10–15 min at 37° C., then centrifuged and washed at least 3 times in normal saline. The pellet was then resuspended in a total volume of 5 ml to make a 2% suspension.

5.2.2 Ficin Treatment of Human RBC

Human Rh$^+$ blood was collected from a blood bank unit in anticoagulant (citrate-phosphate-dextrose) then centrifuged and washed in PBS. One ml of packed RBC was mixed with 1 ml of PBS in a test tube. In a second tube, 2.25 ml PBS and 37.5 mg of Ficin (Sigma Chemical Co., St. Louis, Mo.) was mixed gently. The tubes were incubated separately for 15 min at 37° C. then the contents of the two tubes were mixed and incubated for an additional 15 min. Cells were then centrifuged and washed three times with PBS, and resuspended to a concentration of 2% for use in agglutination assays. Trypsin digestion was utilized in rabbit RBCs and Ficin in human RBCs to expose more of the epitopes which are targets for antibodies, thereby making the assays more sensitive.

5.2.3 General Antigen Extract Analysis Protocol

An inhibition assay was performed for antigen analysis using enzyme-treated RBCs in a 2% suspension in phosphate buffered saline (PBS). The standard antiserum was diluted 1:10 in PBS with 2% normal serum (NS), then 2-fold dilutions were made (i.e., 1:10, 1:20, 1:40, 1:80, etc.). Equal volumes of each diluted serum aliquot and antigen extract adjusted to 1.3 $OD_{280}$ (1 cm path length) were mixed and incubated for 1 hr at 37° C. Controls consisting of EDTA buffer without antigen extracts were prepared in similar fashion. A 50 µl aliquot of each mixture was placed on a glass slide and 50 µl of a 2% RBC suspension in PBS was added. Slides were rotated slowly for 8 min on a LabLine 3D rotator, the highest dilution recording a weak agglutination (anything that appears more agglutinated than the negative control) was scored as the titer.

If the antigen preparation contains active Rh antigen, the titer on the set of tubes mixed with the antigen extract is lower than the titer in the control set due to the binding of soluble antigen and antibody during the 1 hr incubation, and the concomitant reduction in antibody available for agglutinating the enzyme-treated RBCs (FIG. 3).

5.2.4 Antigen Destruction by Metal Salt-Based Buffers

Initial studies showed that the antigenic activity of the Rh antigen was rapidly destroyed when the antigen was exposed to salt buffers. In FIG. 1 the inhibition capacity of the antigen was shown to be destroyed after 16 hr in PBS or in 0.5 M sodium bicarbonate/PBS (a standard buffer for ELISA coating). Additional studies on the stability of the isolated antigen are described below in section 5.9.

5.2.5 Rh Antigen Activity is Buffer Dependent

In FIG. 2, Rh antigen was incubated in the presence of the indicated final concentrations of several buffers, proteins, ampholytes, detergents, zwitterions, etc. for 16 hr and the inhibitory capacity of the mixture on an RBC agglutination reaction was measured. If the added component had no effect on the antigenicity of the Rh antigen, no agglutination would be expected. If the buffer destroyed or diminished Rh antigen antigenicity, an increase in the level of agglutination would be expected. Using EDTA buffer as the 0% (positive) control and a reaction lacking any Rh antigen as the 100% (negative) control, the least destruction of Rh antigen was observed when either 0.5% final concentration of polyethylene glycol 6000 or 2% WRA buffer (pH 7.4) was used to buffer the Rh antigen preparation.

WRA (wide-range ampholyte) buffer was prepared from pentaethylene-hexamine (PEHA) (Aldrich Chemical Co., #29,275-3) and acrylic acid (99+%, Aldrich Chemical Co., #14,723-0) which had been rendered devoid of hydroxyquinone monomethyl ether (HMME). HMME was removed from the commercial source of acrylic acid by passage through a bed of Amberlyst A-27 (Rohm and Haas, Philadelphia, Pa.; Aldrich #21,643-7) according to the manufacturer's instructions at a ratio of 10 ml Amberlyst per 100 ml of acrylic acid.

139.2 ml PEHA was then slowly added to 210 ml of previously-degassed (by boiling) distilled water with constant stirring. 130.34 ml of purified HMME-free acrylic acid was then added to the flask, which was then sealed and gassed thoroughly with dry medical-grade nitrogen and stirred for 16 hr at a constant temperature of 70° C. The solution was then allowed to cool to room temperature. Distilled water was added to bring the total volume to 673 ml, making a 40% (wt/vol) solution. This solution was stored at 4° C. in a brown bottle. In this synthesis, 3.02 moles of acrylic acid was used per mole of PEHA, or 1 mole acrylic acid per 2 moles of PEHA amino groups. Thus approximately 50% of the PEHA amino groups in WRA buffer were substituted with an acid group.

In typical studies, the 40% stock solution of WRA buffer was diluted to a concentration of 3% using distilled water giving a pH of approximately 6.6–7.0. The final working pH was modified using either ethylene diamine (to raise the pH) or propionic acid (to lower the pH).

Since WRA is an amphoteric organic buffer, several other amphoteric buffers were analyzed. FIG. 3 shows comparative results of using several buffers, all at concentrations of 3% compared to the EDTA buffer which served as the 100% uninhibited control. Clearly, all the amphoteric buffers tested including WRA, glycine, HEPES (N-[2-hydroxyethyl] piperazine-N'-[2-ethanesulfonic acid]) and MOPS (3-[N-morpholino]propanesulfonic acid), all at pH 7.4 equally preserved Rh antigen activity.

5.3 Example 3
Methods for Preparing Immobilized Rh Antigen
5.3.1 Coating Beads Glass or plastic beads (50 μm diameter) were washed in EDTA buffer, pH 2.4 and the supernatant was discarded. One ml of bead pellet was mixed with 2 ml Rh antigen of 1.3 $OD_{280}$ units (1 cm path length) which was made 0.2 M in glycine by adding dry glycine and the pH was lowered to 2.4 using 6 M HCl, and the mixture is agitated for 16–48 hr at 4° C. The mixture was centrifuged and washed 3 times, the total volume and final $OD_{280}$ of each supernatant was collected and measured. The total protein recovered in the washes was determined and compared with the total amount of Rh antigen added for determination of adsorption percentage.

5.3.2 Coating ELISA Wells

ELISA wells are coated with 50–75 μl of Rh antigen which was made 0.2 M with respect to glycine and the pH was lowered to 2.4 using 6 M HCl. Plates were incubated for various times (4–16 hr) at various temperatures (room temperature or 4° C.) and the wells were washed with appropriate buffers in preparation for the next reagent.

5.3.3 Results

Studies on pH dependence for coating plastic beads was analyzed. FIG. 4 shows that strict pH dependence was shown with low pH being the preferred pH for coating Rh antigen onto the surface of plastic beads (t-Butyl HIC beads were used). Additional studies with unit pH increments between pH 5.0 and 1.0 confirmed that the peak adsorption efficiency was reached around pH 2.0 (FIG. 5). FIG. 6 shows that the ranges of adsorption efficiencies for 6 separate preparations of Rh antigen isolated in EDTA buffer at pH 7.4 do not even overlap with the range of adsorption efficiencies for 10 different lots of Rh antigen prepared in glycine buffer at pH 2.4. These data confirmed the importance of low pH conditions for the successful preservation of active Rh antigen when immobilizing the antigen to a solid support.

5.3.4 pH Effects are on Rh Antigen and Not on the Adsorbing Matrix

Since many matrices commonly used in the immobilization of antigens are plastic, it was important to determine whether or not the use of such low pH solutions for the immobilization of the active antigen had an effect on the composition of the matrix itself. Polymethylmethacrylate is a polyester, and since esters are known to be hydrolyzable at extreme pH ranges, it was critical to demonstrate that the low pH dependence of Rh antigen adsorption was due to pH effects on the Rh antigen itself, and not merely chemical alteration of the matrix, causing it to become chemically reactive or otherwise modified.

Studies were performed to demonstrate that the low pH used during the immobilization step did not alter the plastics used as matrices. Naked sets of beads were treated with glycine buffers ranging from pH 1.0 to 7.3 overnight with agitation, and then washed in EDTA Buffer (pH 7.4) until the pH of each set was 7.4. Rh antigen in EDTA Buffer, (pH 7.4) was then added and the mixtures were agitated overnight. The sets of beads were then centrifuged and washed 3 times. Each set of supernatants from each bead set was measured for volume and OD and the total percentage of antigen adsorbed to bead sets was determined by subtraction. The results of the study are shown in FIG. 7. Regardless of pretreatment pH between pH 7.3 and 1.9, all bead sets adsorbed about the same percentage of Rh antigen. Thus, the heightened adsorption capacity of Rh antigen on plastic beads at pH 2.4 was an effect on the protein itself, and no an effect of chemically altering the matrix to bind more total protein.

5.3.5 Matrix Compositions Useful for Rh Antigen Adsorption

To demonstrate the wide-range of preferred matrices for use in the practice of the present invention, three different types of plastic beads and glass beads were coated with Rh antigen in glycine buffer at pH 2.4 as described above. All bead types were approximately 50 μm diameter. Following centrifugation and supernatant analysis the percentage of Rh antigen adsorbed to beads was determined by subtraction. FIG. 8 shows that glass beads adsorbed 56% of Rh antigen, the Bio-Rad SM-2 (polystyrene divinylbenzene, catalog #152-3924) adsorbed 62%, Bio-Rad MPE (polymethyl methacrylate) adsorbed 80% and the Bio-Rad 1-Butyl HIC (t-butyl polymethyl methacrylate, catalog #156-0090) were the most efficient, adsorbing 95% of the Rh antigen added.

5.4 Example 4
Methods for Determining Activity of Bound Antigen

The activity of Rh antigen bound to the surface of a solid matrix was determined qualitatively by absorption of anti-Rh antibody from serum. A 2-ml aliquot of serum was diluted to a known titer (i.e., 1:512). One ml of this was mixed with 1 ml packed beads coated with the Rh antigen preparation and 1 ml was mixed with 1 ml packed naked control beads. The mixture was agitated for 2 hr and centrifuged. The supernatant of each sample was then used in a direct agglutination assay. The decrease in titer of the aliquot incubated in the presence of Rh antigen-coated beads was compared to the control.

5.5 Example 5
Methods for Determining Specificity of Bound Rh Antigen

5.5.1 Adsorbed Blood Group Antigens are Immunologically Specific

It is crucial that any antigen coated on a solid surface retain its active conformation, and hence its antigenic specificity if it is to be used for immunoassay or antibody purification purposes. To demonstrate that the novel adsorption methods described herein for immobilizing active Rh antigen did not alter its specificity, studies were conducted which demonstrated the effectiveness of the disclosed methods in preserving antigen specificity. To demonstrate that the methods were also not limited to just one particular blood group antigen, or to one species of animal, two different rabbit antigens and the human Rh D antigen were assayed for specificity following antigen immobilization onto solid support matrices such as plastic beads.

5.5.1.1 Rabbit Allelic RBC Antigens A and F

In one study, plastic beads were coated with rabbit F antigen. One aliquot of naked (uncoated) beads and 2 aliquots of F antigen-coated beads were prepared. An aliquot of each antiserum (anti-A and anti-F) was prepared to give an agglutination titer of 1:640 with homologous RBCs. Aliquots of anti-F were mixed with either control beads (Cx. beads) or F antigen-coated beads. An aliquot of anti-A was also mixed with beads coated with F antigen. The results are shown in FIG. 9.

F antigen-coated beads absorbed anti-F antibodies but not anti-A antibodies (FIG. 9, top 2 bars). Control beads (uncoated) did not absorb anti-F antibodies (FIG. 9, bar 3). Control agglutination reactions are shown in the bottom two bars. Thus, naked beads do not absorb anti-F antibodies, and A antigen-coated beads do not absorb anti-F. Only F antigen-coated beads absorb anti-F antibodies. Thus, antigen specificity is retained after immobilization to a solid substrate.

5.5.1.2 Human Rho(D) Antigen

Antigen extracts from both Rho(D)$^+$ and Rho(D)$^-$ RBCs were prepared. Results demonstrated that the D$^+$ extract inhibited a reaction of each of two monoclonal anti-D reagents with D+ ficin-coated RBC but the D− extract did not inhibit the reactions. Each extract was then coated on t-Butyl HIC beads at pH 2.4 in glycine buffer and washed. Each mAb had an agglutination titer of 1:1,280 with D+ RBCs (FIG. 10, bars 3 and 6 from the top). When aliquots of mAb1 and mAb2 were mixed with aliquots of D+ extract-coated beads, the titers of supernatants dropped to 1:40 (FIG. 10, bars 1 and 4 from the top). When identical aliquots of mAb1 and mAb2 were mixed with identical aliquots of D− extract-coated beads the titers were unchanged from control levels (FIG. 10, bars 2 and 5 from the top). Thus, antigen specificity was also maintained after adsorption of human blood group antigens to a matrix.

The conclusion from both the rabbit and human specificity studies is that the antigens do not become non-specifically sticky for random antibodies upon adhering to a solid phase support. Instead, immunological specificity is retained.

5.5.2 Adsorbed Blood Group Antigens Retain a High Degree of Antigenicity

Although it was shown in 5.5.1 that antigen extracts from an RBC population (as defined by $OD_{280}$) remain active and specific when adsorbed to a solid support in a pH-dependent manner, the inventors have also demonstrated that the adsorbed protein retains a high degree of antigenic activity even after undergoing a low-pH adsorption.

Bio-Rad t-Butyl HIC beads were coated with rabbit F antigen at pH 2.4, 7.4 and 11.0 and washed. Naked beads were used as a control. Anti-F serum was diluted to give a titer of 1:1,280 after absorption with naked beads (FIG. 11, bottom bar). After absorption of identical aliquots of anti-F with beads coated at pH 2.4, 7.4 and 11.0, the supernatants gave agglutination titers as shown in FIG. 11. Although beads coated at pH 11.0 and 7.4 removed some antibodies, the beads coated with an antigen composition at pH 2.4 absorbed the anti-F antibodies completely. This shows that the antigen composition coated at pH 2.4 is clearly more antigenically-active than the antigen composition coated at pH 7.4 or 11.0 in absorbing specific antibodies from anti-serum.

5.6 Example 6

Isolation of Blood Group Antigen-Specific Antibodies 5.6.1 Methods for Isolating anti-Rh Antibodies Using Immobilized Rh Antigen To demonstrate the utility of the disclosed antigen compositions in removing specific antibodies from solution, devices and methods were developed which permit the ready isolation of antibodies specific for particular blood group antigens from solution. In a preferred embodiment, such devices and methods are useful for the removal of anti-Rh antibodies from the plasma of a pregnant female.

In these studies, one volume of t-Butyl HIC beads was coated with 2 volumes of Rh antigen and washed in EDTA buffer, pH 7.4. The coated beads were then packed into a column to provide a device for the removal of antibodies from solution. One volume of an immune serum solution was passed through the column and then the column was washed with 0.1 M glycine, pH 7.4, until the $OD_{280}$ dropped to a baseline level. Several volumes of 3 M ammonium thiocyanate were passed through the device and the eluate was recovered, dialyzed exhaustively against PBS to remove the thiocyanate, and then quantitated by spectrophotometry at 280 nm to determine protein content.

In the routine practice of the invention, the inventors have demonstrated that the serum used may either be intact serum, concentrated serum, or diluted in any of the zwitterionic buffers disclosed herein. The protocol may also be used for either polyclonal or monoclonal antibodies.

5.6.2 Compositions for Eluting Antibodies from Devices

In addition to the methods described in 5.6.1, the inventors have demonstrated that various eluting buffers may be used in the routine practice of the invention to recover antibodies once bound to the solid-phase antigen compositions.

In sharp contrast to the teachings of the prior art, however, the inventors have found that low-pH glycine buffer (a universally-used means of eluting antibodies from solid state supports) was completely ineffective as an elution agent using the compositions, methods, and devices described herein. Elution attempts with low-pH glycine buffers eluted almost no detectable antibodies.

To that end, the inventors investigated the use of chaotropic reagents and high-pH solutions for successful elution of the antibodies. In one particular study, Bio-Rad t-Butyl HIC beads were coated with rabbit F antigen and aliquotted into three test tubes. Anti-F antiserum was added to each aliquot of beads, and the beads were thoroughly washed by centrifugation. Each aliquot of beads was then treated with three eluting agents (3 M ammonium thiocyanate, pH 4.5; 200 mg/ml chloroquin diphosphate; NaOH solution at pH 11.5). Supernatants were exhaustively dialyzed against PBS and each supernatant was then titrated using trypsinized F-containing RBCs. These data (shown in FIG. 12) showed that naked beads mixed with antibody did not absorb any antibody elutable with thiocyanate, and that thiocyanate was the most efficient eluant.

In this study, HIC beads were coated with antigen in EDTA buffer, pH 7.4, and it was determined that 56% of the antigen bound to the beads. One ml coated beads were mixed with 2 ml anti-F having a neat titer of 1:2,560 and the beads were then centrifuged. Antibodies were eluted with 4 ml of 0.2 M glycine, pH 2.4 at 37° C. for 2 hr. The eluate was exhaustively dialyzed versus PBS. Agglutination assays of this first eluate were weakly positive only with undiluted eluate. Supernatant titer of serum after mixing with beads was 1:160 compared with a control (absorbed using 1 ml naked beads) that was 1:1,280. The same beads were mixed with a second aliquot of fresh anti-F after washing them in WRA buffer. These beads were mixed with 1 ml of anti-F diluted to a titer of 1:256 in WRA buffer for 1 hr at 37° C. These beads were centrifuged and washed in WRA buffer. The beads were incubated at 37° C. for 2 hr in 4 ml of 0.2 M glycine, pH 2.4. After centrifugation, the supernatant was exhaustively dialyzed against PBS. Agglutination assays of the second supernatant after dialysis were negative. Supernatant titer of serum after mixing with beads the second time was now 1:80 indicating that a small additional amount of antibody was absorbed the second time but that beads were likely saturated with antibody since some of the antibody did not bind. Due to dilution, the second supernatant would have been 1:128 if no antibody had been absorbed.

The clear result was that 0.2 M glycine, pH 2.4 eluted virtually no antibody from antigen-coated, beads which were shown to bind antibody. This was in sharp contrast to the data obtained when chaotropic and/or high pH buffers were utilized. This method represents the first known incidence of an antigen-antibody system which appears to be non-susceptible to the acid elution methods routinely used in the art for the elution of antibodies from a solid antigen support system.

5.7 Example 7

Methods for Determining Stability of Immobilized Antigen 5.7.1 Stability of Bound Rh Antigen in the Presence of 3 M Thiocyanate It was important to determine if the adsorbed blood group antigen remained adhered to the solid support during antibody elution steps, since elution of both Ab and antigen would create undesirable antigen-antibody complexes in solution, and would not result in separation of the antibody from its corresponding antigen.

Bio-Rad t-Butyl HIC beads were coated with rabbit F antigen. It was determined that aliquots of beads had adsorbed a total of 0.85 $OD_{280}$ units of antigen (FIG. 13, top bar). The supernatant of an aliquot of beads which had been mixed with anti-F antibodies and eluted with thiocyanate had an $OD_{280}$ of 0.526 following dialysis in PBS (FIG. 13, second bar from top), while supernatants from either antigen-coated beads lacking antibody treatment or naked control beads alone had negligible $OD_{280}$ after dialysis (FIG. 13, bars 3 and 4 from top). These results indicated that chaotropic buffers (such as 3 M ammonium thiocyanate) successfully eluted antibodies from antigen-coated beads, but did not co-elute the antigen itself.

5.7.2 Antibody Yield After Thiocyanate Elution, Titer and Mass

From these data it was clear that protein (defined as $OD_{280}$) was eluted from antigen-coated beads after mixing those beads with antiserum and that no protein was eluted from antigen-coated beads which had not been incubated previously with antiserum. The supernatants from each of the three eluates were tested by agglutination versus trypsinized F RBCs after dialysis against PBS. FIG. 14 shows that the thiocyanate 5, eluate from beads coated at pH 2.4 had a titer of 1:32 whereas the pH 7.4 eluate had a titer of 1:2 and the pH 11 eluate had no detectable antibody content. Eluates of naked beads also had no detectable agglutination titer. Thus, eluate from beads coated with antigen compositions at pH 2.4 retained substantial antibody activity.

The protein content of each sample was determined by measuring the optical density at 280 nm ($OD_{280}$). As shown in FIG. 15, the supernatant of the pH 2.4 aliquot had an $OD_{280}$ of 1.948 and the other supernatants had dramatically lower $OD_{280}$. This confirms that the eluate recovered in the pH 2.4/thiocyanate elution protocol had both the highest antibody activity and the highest total mass recovered of the three samples.

5.8 Example 8
ELISA Methods and Compositions
5.8.1 ELISA Compositions for Blood Group Antigens In these studies, all adsorption of blood group antigens onto solid surfaces was done in 0.1 M glycine buffer, pH 2.4. All washing steps were done preferably using 0.1 M glycine buffer, pH 7.4, although salt buffers such as PBS were equally useful for shortened protocols where bound antigen was not in contact with the buffer for periods longer than 4–6 hr. Wash steps optionally included the addition of 0.05–1% Tween-20 to the buffer. A blocking step is also optional, but if used, the blocking agent may be any of a whole range of commonly-used agents such as bovine serum albumin, human serum albumin, hen egg ovalbumin, and milk proteins such as casein, etc. The developing anti-Ig antibody may be of goat, sheep, or rabbit, etc. origin. It should be broadly specific for IgG Fc of all 4 subclasses but for some applications might be specific for $IgG_1$, $IgG_2$, $IgG_3$, or $IgG_4$. The antibody may be conjugated with horseradish peroxidase, alkaline phosphatase, or any other suitable enzyme. For RIA analysis, the developing antibody may be conjugated with $^{125}I$, $^{131}I$ or any other suitable radionuclide.

Standard ELISA plates (Immulon II™) were coated with 50 μl of either human $D^+$ or $D^-$ RBC extracts overnight in glycine buffer at pH 2.4. Plates were washed, blocked with 1% human serum albumin, washed, and serial dilutions of mAb1 were added to duplicate wells. After 2 hr incubation, wells were washed and 50 μl of a 1:2,000 dilution of peroxidase-conjugated goat anti-human IgG (H-chain specific) was added. After 2 hr incubation, the wells were washed and substrate ABTS (Boehringer-Mannheim, 2,2'-azino-di-[3-ethylbenzthiazoline sulfonate] diammonium salt) was added. After 30 min, 50 μl of 2 M $H_2SO_4$ was added to stop the reaction. The results are shown in FIG. 16. The $D^-$-coated wells showed only background level reactivity. Thus, human $D^+$ antigen extracts effectively coated matrices for use in ELISA methods.

Similar methods were used to coat ELISA plates with rabbit F antigen in glycine, pH 2.4. Peroxidase-conjugated goat anti-rabbit IgG Fc was used. The results shown in FIG. 17 indicated that a typical ELISA format dilution curve was also obtained when using rabbit blood group antigen extracts.

5.8.2 Analysis of Rh Antigens and Blood Group Antigens M and S

Studies of an antigen composition isolated from human RBCs having the phenotype D, C, c, e, K, k, Fya, Fyb, Jka, Jkb, s, M, N, Pi, Leb were performed. The method used was to first coat the wells of polystyrene U-bottom plates with 75 μl of antigen extract in glycine buffer, pH 2.4. Identical plates were incubated 4 hr at 37°, 25° and 4° C. After washing, 50 μl of monoclonal antibody was added at 37° C. for 15 min and the plates were then washed repeatedly with PBS. 50 μl of ficin-treated RBCs were then added to each well and the RBCs were allowed to settle out at room temperature. The presence of bound antibody (positive reaction) was determined by adherence of the ficin-treated indicator cells over the surface of the well due to bridging. The absence of antibody binding (negative reaction) was indicated by pelleting of the ficin-treated RBCs into a pellet in the bottom of the microtiter plate well. The results of the assays are shown in Table 2. The results show that adsorption efficiency was not temperature-dependent for the range of about 4 to about 37° C.

TABLE 2

Analysis of Human RBC Extract and Effects of Adsorption Temperature

|  | 4° C. | 25° C. | 37° C. |
| --- | --- | --- | --- |
| Anti-D | + | + | + |
| Anti-C | 0 | 0 | 0 |
| Anti-c | w+ | w+ | w+ |
| Anti-E | + | + | + |
| Anti-e | + | + | + |
| Anti-M | 0 | 0 | 0 |
| Anti-S | 0 | 0 | 0 |

Phenotype: D, C, c, e, K, k, Fya, Fyb, Jka, Jkb, s, M, N, Pl, Leb

Moreover, these data also demonstrated that the D, c, and e antigens were detected in the antigen extract preparation. While the C antigen (reportedly present on the RBCs tested) was not detected during this study, it is not known whether such inability to detect the C antigen was due to a pH lability of the antigen itself, or either mis-typing of the particular lot of RBCs used in the study. Likewise, the reason for the unexpected reaction of anti-E may also be due to an initial mis-typing of the RBC preparation, or non-specificity of the anti-E antibody employed. Regardless, the data show that the present methods and compositions are successful for a wide-range of Rh blood group antigens from both animal and human sources, and are not limited to Rh D antigen alone.

5.8.3 Stability of Immobilized Antigen—Drying and Rehydration Studies

The antigen compositions described herein were also used to coat plates for drying and rehydration studies. Plates were coated for 4 hr with antigen in glycine, pH 2.4 at 25° C. Plates were washed with PBS and then 100 μl of Immucor(D drying agent (Immucor, Inc., Norcross, Ga.), 5% WRA anphoteric buffer, or nothing (not even water) was added. The plates were then patted dry on a paper towel. The plates were placed in a foil pouch (forms a complete water barrier) with desiccant to remove water and a moisture indicator, sealed, and placed at 4° C. After 48 hr, plates were analyzed using monoclonal antibodies as described above. The results shown in Table 3 indicate that the D, c and e antigens were antigenically equal to freshly prepared plates (column marked "fresh").

TABLE 3

Effects of Drying on Human RBC Extracts

|  | Immucor ® | 5% WRA | Nothing | Fresh |
|---|---|---|---|---|
| Anti-D | + | + | + | + |
| Anti-C | 0 | 0 | 0 | 0 |
| Anti-c | + | + | + | w+ |
| Anti-E | + | + | + | + |
| Anti-e | + | + | + | + |
| Anti-Jka | 0 | 0 | 0 | 0 |
| Anti-Jkb | 0 | 0 | 0 | 0 |

The only exception was that the c antigen seemed slightly stronger in the 3 dried plates than in the freshly prepared plate. Again the E antigen was detected and C was not, as was discussed in the previous section. These results show that the methods for isolating active blood group antigens give rise to antigenic compositions which may be successfully dried and rehydrated 48 hr after coating on plastic surfaces. Surprisingly, the Kidd blood group antigens present in the original RBC preparation were not detected in the extracts, even when freshly-prepared plates were utilized.

Other studies were done to determine the length of time that the dried antigen was stable and could be successfully rehydrated. The plates were coated with acidified antigen compositions at different concentrations. Wells were coated with concentrations of antigen extracts ranging from 500 μg/ml down to 15.6 μg/ml. 100 μl was added/well, and plates were dried as above. The plates were rehydrated and then analyzed as described above.

Results after dry storage for 2 days and for 5 weeks are described in Tables 4–9 for each of three preparations of different beginning phenotypes.

These results show that the antigen compositions isolated using the methods described herein from three different phenotypes maintains antigenic stability for up to 5 weeks after drying. In nearly all cases only a 1 tube drop in concentration was evident after 5 weeks of total dryness. The c, e cell antigen compositions showed the greatest specificity with the least non-specific reactivity. As in other assays, the anti-E reacted nonspecifically with D, C, c, e and D, D, e cell extracts, but not with c, e antigen compositions. This could indicate a similarity in epitopes of D and E revealed by drying. An alternative is that the acidic treatment is denaturing E antigen to be nonspecifically reactive with this particular monoclonal anti-D. Regardless, the clearest result is that antigen compositions can be successfully dried onto the surface of plastic plates and retain major antigenic reactivity after at least 5 weeks in the dry state. These results indicate a significant improvement over the current state of the art where stable pre-coated ELISA matrices are not available for blood group antigens such as the $Rh_o(D)$ factor.

TABLE 4

D, C, c, e Cell Antigen Extract After 48 hr

Concentration of AX Added to Wells During Coating at pH 2.4 (μg/ml)

|  | 500 | 250 | 125 | 62.5 | 31.25 | 15.62 |
|---|---|---|---|---|---|---|
| Anti-D | + | + | + | + | +/− | 0 |
| Anti-C | 0 | 0 | 0 | 0 | 0 | 0 |
| Anti-c | + | + | + | + | + | +/− |
| Anti-E | + | + | + | + | + | +/− |
| Anti-e | + | + | + | + | +/− | 0 |

TABLE 5

D, C, c, e Cell Antigen Extract After 5 Weeks

Concentration of AX Added to Wells During Coating at pH 2.4 (μg/ml)

|  | 500 | 250 | 125 | 62.5 | 31.25 | 15.62 |
|---|---|---|---|---|---|---|
| Anti-D | + | + | + | +/− | 0 | 0 |
| Anti-C | 0 | 0 | 0 | 0 | 0 | 0 |
| Anti-c | + | + | + | + | +/− | 0 |
| Anti-E | + | + | + | + | +/− | 0 |
| Anti-e | + | + | + | + | +/− | 0 |

TABLE 6

D, C, e Cell Antigen Extract After 48 hr

Concentration of AX Added to Wells During Coating at pH 2.4 (μg/ml)

|  | 500 | 250 | 125 | 62.5 | 31.25 | 15.62 |
|---|---|---|---|---|---|---|
| Anti-D | + | + | + | + | + | + |
| Anti-C | 0 | 0 | 0 | 0 | 0 | 0 |
| Anti-c | + | + | + | + | 0 | 0 |
| Anti-E | + | + | + | + | + | +/− |
| Anti-e | + | + | + | + | +/− | 0 |

TABLE 8 c, e Cell Antigen Extract After 48 hr

Concentration of AX Added to Wells During Coating at pH 2.4 (μg/ml)

|  | 500 | 250 | 125 | 62.5 | 31.25 | 15.62 |
|---|---|---|---|---|---|---|
| Anti-D | + | +/− | 0 | 0 | 0 | 0 |
| Anti-C | +/− | +/− | 0 | 0 | 0 | 0 |
| Anti-c | + | + | + | + | + | + |
| Anti-E | +/− | 0 | 0 | 0 | 0 | 0 |
| Anti-e | + | + | + | + | + | +/− |

TABLE 7

D, C, e Cell Antigen Extract After 5 Weeks

Concentration of Ax Added to Wells During Coating at pH 2.4 (µg/ml)

|        | 500 | 250 | 125 | 62.5 | 31.25 | 15.62 |
|--------|-----|-----|-----|------|-------|-------|
| Anti-D | +   | +   | +   | +    | +/−   | 0     |
| Anti-C | +/− | 0   | 0   | 0    | 0     | 0     |
| Anti-c | +   | +   | +   | +    | 0     | 0     |
| Anti-E | +   | +   | +   | +/−  | 0     | 0     |
| Anti-e | +   | +   | +   | +/−  | 0     | 0     |

TABLE 9 c, e Cell Antigen Extract After 5 Weeks

Concentration of AX Added to Wells During Coating at pH 2.4 (µg/ml)

|        | 500 | 250 | 125 | 62.5 | 31.25 | 15.62 |
|--------|-----|-----|-----|------|-------|-------|
| Anti-D | 0   | 0   | 0   | 0    | 0     | 0     |
| Anti-C | +/− | 0   | 0   | 0    | 0     | 0     |
| Anti-c | +   | +   | +   | +    | 0     | 0     |
| Anti-E | 0   | 0   | 0   | 0    | 0     | 0     |
| Anti-e | +   | +   | +   | +    | +     | +/−   |

5.9 Example 9

Methods for Long-Term Storage of Active Rh Antigen

5.9.1 Stability of Antigen Compositions in EDTA Buffer at 4° C.

Several lots of rabbit RBC antigen compositions have been stored in EDTA buffer for various periods of time at 4° C. and analyzed for their ability to inhibit an Ab-RBC reaction. The results are shown in Table 10. These data clearly show that the compositions disclosed are stable at 4° C. for at least 47 days when stored in EDTA buffer.

TABLE 10

Stability of Rh antigen in EDTA Buffer at 4° C.

| Antigen Type | Date Prepared | Initial Inhibition | Later Inhibition | Age of Antigen |
|---|---|---|---|---|
| A | 10/12/95 | 640 to 160 | 2,560 to 320 | 47 days |
| A | 10/26/95 | 640 to 640 | 2,560 to 320 | 33 days |
| F | 11/02/95 | 640 to 160 | 2,560 to 160 | 27 days |

5.9.2 Stability of Soluble Rabbit RBC Antigen Compositions

One ml aliquots of rabbit blood group F antigen extract (AgX) was mixed with an equal volume of the buffers shown in the legend of Table 11. Buffers were initially at a concentration twice that shown in the legend. In Tables 12 and 13, the pH was adjusted to either pH 4.5 or pH 2.4 as indicated. Incubations of the mixtures were done at room temperature for the times indicated (4 hr, 24 hr 48 hr, 96 hr, and 192 hr). At the end of the incubations, the samples were used as inhibitors in a standard agglutination assay. In Tables 12 and 13, the pH of the EDTA controls were 4.5 and 2.4, respectively.

TABLE 11

Stability of Rabbit RBC Antigen Extract -- Soluble Extract--Neutral pH

| Buffer* | 4 hr | 24 hr | 48 hr | 96 hr | 192 hr |
|---|---|---|---|---|---|
| WRA | 80# | 80 | 80 | 80 | 80 |
| Glycine | 80 | 160 | 160 | 160 | 160 |
| HEPES | 160 | 160 | 320 | 320 | 640 |
| MOPS | 320 | 320 | 640 | 640 | 640 |
| Bis-Tris | 80 | 80 | 80 | 80 | 160 |
| Bis-Propane | 160 | 160 | 320 | 320 | 640 |
| Alanine | 160 | 160 | 160 | 160 | 320 |
| Pharmalyte | 80 | 160 | 160 | 160 | 160 |
| Saline | 80 | 160 | 160 | 160 | 320 |
| Borate | 1280 | 1280 | 1280 | 1280 | 1280 |
| Phosphate | 160 | 320 | 320 | 320 | 320 |
| Sod. Bicarbonate | 1280 | 1280 | 1280 | 1280 | 1280 |
| Acetate | 80 | 160 | 160 | 160 | 320 |
| EDTA/AgX | 80 | 80 | 80 | 80 | 80 |
| EDTA no X | 640 | 640 | 640 | 640 | 1280 |

*Buffers/pH/final concentrations: WRA, wide range ampholytes, pH 7.4, 1.5%; Glycine, glycine-HCl, pH 6.3, 1.5%; HEPES, N-(2-hydroxyethyl)piperazine-N'-(2-ethanesulfonic acid), pH 5.6, 1.5%; MOPS, 3-(N-morpholino)propanesulfonic acid, pH 5.4, 1.5%; Bis-Tris, (bis[2-hydroxyethyl]imino-tris[hydroxymethyl]methane), pH 8.8, 1.5%; Bis-Propane, (1,3-bis[tris(hydroxymethyl)methylamino]-propane), pH 9.3, 1.5%; Alanine, alanine-HCl, pH 7.1, 1.5%; Pharmalyte ™, Pharmacia brand ampholytes, pH 7.1, 1.5%; Saline, NaCl, pH 6.3, 0.85%; Borate, boric acid/NaOH/NaCl, pH 8.0, 0.15 M; Phosphate, $NaH_2PO_4/K_2HPO_4$, pH 7.0, 0.15 M; Sod. Bicarbonate, sodium bicarbonate, pH 8.1, 0.25 M; Acetate, sodium acetate, pH 7.7, 0.15 M. EDTA/AgX is antigen extract in EDTA. EDTA no X is the EDTA buffer only control, no antigen extract added.
Values are inverse titer values, i.e. a 1:80 dilution is entered as 80.

TABLE 12

Stability Of Rabbit RBC Antigen Extract -- Soluble Extract--pH 4.5

| Buffer* | 4 hr | 24 hr | 48 hr | 96 hr | 192 hr |
|---|---|---|---|---|---|
| WRA | 160# | 320 | 320 | 320 | 320 |
| Glycine | 640 | 1280 | 1280 | 1280 | 1280 |
| HBPES | 160 | 320 | 640 | 640 | 640 |
| Bis-Tris | 320 | 640 | 640 | 1280 | 1280 |
| Saline | 320 | 640 | 640 | 640 | 640 |
| Borate | 1280 | 1280 | 1280 | 1280 | 2560 |
| Sod. Bicarb. | 1280 | 1280 | 1280 | 1280 | 2560 |
| Acetate | <5 | <5 | <5 | <5 | <5 |
| EDTA/AgX | 80 | 160 | 160 | 160 | 160 |
| EDTA no X | 1280 | 2560 | 2560 | 2560 | 1280 |

*Buffers at the following concentrations, all adjusted to pH 4.5: WRA, Glycine, HEPES, and Bis-Tris at 1.5%, Saline is 0.85% NaCl, Bicarbonate is 0.25 M, Acetate is 0.15 M.
Inverse titer data reported as described in Table 11.
EDTA/AgX is antigen extract in EDTA. EDTA no X is the BDTA buffer only control, no antigen extract added.

TABLE 13

Stability of Rabbit RBC Antigen Extract -- Soluble Extract--pH 2.4

| Buffer* | 4 hr | 24 hr | 48 hr | 96 hr | 192 hr |
|---|---|---|---|---|---|
| WRA | <5# | <5 | <5 | <5 | <5 |
| Glycine | Hemolyzed | Hemolyzed | Hemolyzed | Hemolyzed | Hemolyzed |
| HEPES | <5 | <5 | <5 | <5 | <5 |
| Bis-Tris | 1280 | 1280 | 1280 | 1280 | 1280 |

TABLE 13-continued

Stability of Rabbit RBC Antigen Extract -- Soluble Extract--pH 2.4

| | Time of Incubation | | | | |
|---|---|---|---|---|---|
| Buffer* | 4 hr | 24 hr | 48 hr | 96 hr | 192 hr |
| Saline | 2560 | 1280 | 2560 | 2560 | 2560 |
| Borate | 2560 | 2560 | 2560 | 2560 | 2560 |
| Bicarbonate | 2560 | 2560 | 2560 | 2560 | 2560 |
| Acetate | <5 | <5 | <5 | <5 | <5 |
| EDTA/AgX | 640 | 320 | 320 | 640 | 640 |
| EDTA no X | 1280 | 640 | 640 | 640 | 640 |

*Buffers were at the following concentrations, all adjusted to pH 2.4: WRA, Glycine, HEPES, and Bis-Tris @ 1.5%, Saline is 0.85% NaCl, Bicarbonate is 0.25 M, Acetate is 0.15 M.
Inverse titer data reported as described in Table 11
EDTA/AgX is antigen extract in EDTA. EDTA no X is the EDTA buffer only control, no antigen extract added.

5.9.3 Bound Antigen Studies

Bio-Rad HIC beads, 50 μm, were coated with antigen extract (AgX) overnight in glycine buffer, pH 2.4. After washing in EDTA buffer, a 3 ml aliquot of beads was suspended in the Test Buffers and incubated at room temperature for the indicated times. At 15 the end of incubation, 0.5 ml aliquots of packed beads were withdrawn at different times and washed in EDTA buffer, pH 7.0, and the aliquots were then mixed with an equal volume of antiserum. The tubes containing beads and antiserum were agitated to thoroughly mix the contents and the tubes were incubated at 37° C. for 2 hr. The tubes were then centrifuged and the supernatants were titered. Data are shown in Tables 14, 15 and 16.

TABLE 14

Stability of Rabbit RBC Antigen Extract
Antigen Bound to Bio-Rad HIC Beads--Neutral pH

| | Time of Incubation | | | | |
|---|---|---|---|---|---|
| Buffer* | 4 hr | 24 hr | 48 hr | 96 hr | 192 hr |
| WRA | 80# | 80 | 80 | 80 | 80 |
| Glycine | 40 | 40 | 40 | 40 | 40 |
| HEPES | 20 | 20 | 20 | 40 | 40 |
| MOPS | 40 | 40 | 40 | 80 | 80 |
| Bis-Tris | 80 | 80 | 80 | 80 | 80 |
| Bis-Propane | 160 | 320 | 320 | 320 | 320 |
| Alanine | 40 | 40 | 20 | 20 | 40 |
| Pharmalyte | 160 | 160 | 160 | 160 | 160 |
| Saline | 40 | 80 | 80 | 80 | 80 |
| Borate | 160 | 320 | 320 | 320 | 320 |
| Phosphate | 160 | 160 | 160 | 160 | 160 |
| Sod. Bicarb. | 640 | 320 | 320 | 320 | 640 |
| Acetate | 20 | 20 | 20 | 20 | 20 |
| EDTA Std. | 20 | 20 | 40 | 40 | 40 |
| Noncoated | 640 | 640 | 640 | 320 | 640 |

Inverse titer data reported as described in Table 11.
Values are inverse titer values, i.e. a 1:80 dilution is entered as 80.
The EDTA Std. is the bound antigen in EDTA buffer only at neutral pH. Non-coated is the control consisting of non-antigen-coated beads, i.e. the negative control.

TABLE 15

Stability of Rabbit RBC Antigen Extract
Antigen Bound To Bio-Rad HIC Beads--pH 4.5

| | Time of Incubation | | | | |
|---|---|---|---|---|---|
| Buffer* | 4 hr | 24 hr | 48 hr | 96 hr | 196 hr |
| WRA | 20# | 40 | 10 | 10 | 5 |
| Glycine | <5 | <5 | 10 | 10 | 5 |
| HEPES | <5 | 5 | <5 | <5 | <5 |
| Bis-Tris | 10 | 10 | 5 | <5 | 5 |
| Saline | <5 | 10 | <5 | 5 | 10 |
| Borate | <5 | 20 | 10 | 10 | 5 |
| Bicarb. | 5 | 20 | 5 | 5 | 5 |
| Acetate | 20 | 80 | 80 | 80 | 40 |
| EDTA Std. | <5 | 10 | <5 | 5 | 10 |
| Non-coated | 2560 | 2560 | 2560 | 2560 | 2560 |

*Buffers at the following concentrations, all adjusted to pH 4.5: WRA, Glycine, HEPES, and Bis-Tris at 1.5%, Saline is 0.85% NaCl, Bicarbonate is 0.25 M, Acetate is 0.15 M.
The EDTA Std. is the bound antigen in EDTA buffer at pH 4.5. Noncoated is the control of non-antigen-coated beads, i.e. the negative control.
Inverse titer data reported as described in Table 11.

TABLE 16

Stability of Rabbit RBC Antigen Extract
Antigen Bound to Bio-Rad HIC Beads--pH 2.4

| | Time of Incubation | | | | |
|---|---|---|---|---|---|
| Buffer* | 4 hr | 24 hr | 48 hr | 96 hr | 192 hr |
| WRA | 80# | 80 | 40 | 20 | 20 |
| Glycine | 2560 | 1280 | 2560 | 320 | 160 |
| HEPES | 80 | 20 | 20 | 10 | 20 |
| Bis-Tris | 40 | 10 | 5 | 5 | 5 |
| Saline | 10 | 10 | 10 | 10 | 10 |
| Borate | 10 | 10 | 10 | 10 | 10 |
| Bicarb. | 10 | 20 | 10 | 5 | 5 |
| Acetate | 1280 | 320 | 640 | 320 | 160 |
| EDTA Std. | 10 | 20 | 10 | 10 | 20 |
| Noncoated | 2560 | 2560 | 2560 | 2560 | 2560 |

*Buffers at the following concentrations, all adjusted to pH 2.4: WRA, Glycine, HEPES, and Bis-Tris @ 1.5%, Saline is 0.85% NaCl, Bicarbonate is 0.25 M, Acetate is 0.15 M.
The EDTA Std. is the bound antigen in EDTA buffer at pH 2.4. Noncoated is the control of non-antigen-coated beads, i.e. the negative control.
Inverse titer data reported as described in Table 11.

5.9.4 Coating Step Studies

One ml aliquots of Bio-Rad HIC beads, 50 μm, were washed in EDTA buffer. Mixtures consisting of 2 ml of AgX from rabbit F RBC in EDTA buffer and 2 ml Test Buffer at 2× concentration at pH 2.4 were made and added to washed beads. The mixture was incubated overnight at 4° C. with constant agitation. The following morning, the tubes were centrifuged. The supernatants were saved. The beads were washed 2× with EDTA buffer and the supernatants were also saved. The beads were then washed 2× with 0.1 M glycine buffer, pH 7.0. The bead pellet was then mixed with 1 ml of anti-F antiserum and incubated at 37° C. for one hour with occasional agitation. The tubes were then centrifuged and the supernatant was removed and titered. Data are shown in Table 17. Thus, a reduction in titer would indicate the presence of functional antigen on the beads and no reduction in titer would indicate the presence of inactive antigen or that antigen was not absorbed to beads. However, as is readily apparent in Table 8, all preparations adsorbed antigen in three separate experiments with adsorption amounts ranging from approximately 55–94%. Therefore, the inability of beads coated with antigen using buffers other than WRA or Glycine was due to the antigen coating being nonfunctional, inactive antigen caused by the chemical nature of the buffer used.

TABLE 17

Buffer Composition Effects for Coating Bio-Rad HIC Beads at pH 2.4

| Buffer* | Titer# |
|---|---|
| WRA | 64 |
| Glycine | 32 |
| HEPES | 256 |
| Bis-Tris | 512 |
| Saline | 512 |
| Borate | 512 |
| Bicarbonate | 256 |
| Acetate | 512 |
| Noncoated Beads | 512 |

*Buffers at the following final concentrations, all adjusted to pH 2.4: WRA, Glycine HEPES, and Bis-Tris at 1.5%, Saline is 0.85% NaCl, Bicarbonate is 0.25 M, Acetate is 0.15 M.
Inverse titer data reported as described in Table 11.

5.9.4 Stability of Soluble Rabbit RBC Antigen Compositions

In general, the soluble antigens were more sensitive to buffer variations than the bound antigen, regardless of pH. At the higher pH ranges in Table 11 the antigens are much less stable in salt buffers (borate, phosphate, bicarbonate) than in the other buffers tested. The most preferred buffers for maintaining the antigenic activity of the soluble antigen extract at neutral pH were WRA, Bis-Tris, and the EDTA buffer, although the Pharmacia Pharmalyte buffers were also useful in maintaining antigenic activity, albeit at a lesser degree than the most preferred buffers. Other buffers such as alanine, glycine, HEPES, MOPS and Bis-Propane were more destructive than WRA at neutral pH, but were generally less destructive than salt buffers and saline. Thus, WRA, Bis-Tris, and EDTA are the most preferred buffers for maintaining antigenic activity of the soluble form of the antigen extract at the upper end of the pH range.

However, at low pH, significant differences were noted. Only HEPES, WRA, and acetate buffers at pH 2.4, maintain the stability of the antigen (Table 13). All the other buffers, salt based or zwitterionic, damage the antigen. The results at pH 4.5 are intermediate in most cases, except for acetate which is highly protective even at pH 4.5 (Table 12).

5.9.5 Stability of Rabbit Rh Antigen Compositions During Coating Step

Notably, only WRA and glycine buffers at pH 2.4 provide acceptable chemical conditions for the coating step that results in functional antigen coated on the beads (Table 17). All other buffers tested destroy the antigen although they allow the antigen to be coated onto the beads (Table 18).

TABLE 18

Quantitative Adsorption of Rabbit F Antigen to Bio-Rad HIC Beads at pH 2.4

| Buffer* | Study 1 | Study 2 | Study 3 |
|---|---|---|---|
| WRA | 79.9# | 77.2 | 74.3 |
| Glycine | 92.1 | 89.4 | 94.2 |
| HEPES | 90.3 | 87.2 | 93.7 |
| Bis-Tris | 76.8 | 54.5 | 81.2 |
| Saline | 65.8 | 72.8 | 70.8 |
| Borate | 72.5 | 73.0 | 71.7 |
| Bicarbonate | 68.8 | 75.1 | 80.4 |
| Acetate | 82.2 | 74.4 | 86.6 |

*Buffers at the following concentrations, all adjusted to pH 2.4: WRA, Glycine, HEPES, and Bis-Tris at 1.5%, Saline is 0.85% NaCl, Bicarbonate is 0.25 M, Acetate is 0.15 M.
Numbers are percentages of total antigen protein added to the beads which adsorbed to the bead preparation. This was determined spectrophotometrically at 280 nm by subtraction of recovered protein from the amount initially added. Three separate studies were performed over the course of three weeks' time to assess the adsorption

5.9.6 Stability of Rabbit RBC Bound Antigen Compositions

For the most part, the Rh antigen was stabilized after binding to solid surfaces as compared to the soluble form and is more stable at any pH tested when bound than is the soluble counterpart at a given pH. With the notable exceptions of glycine and acetate buffers, the antigenic properties of the bound Rh antigen compositions are largely unaffected by the buffers studied (Table 14, 15 and 16). The destructive effects of glycine and acetate at pH 2.4 were noted to decrease with time.

These data suggest that the Rh antigen compositions of the present invention should be stored before use at neutrality in WRA, Bis-Tris or merely in the EDTA buffer used in the extraction step, be coated onto plates or beads only in WRA or glycine buffers at pH 2.4, and the bound antigen can then be exposed to biological or immunological reagents at neutral pH in a wide array of buffers such as WRA, glycine, HEPES, MOPS, Bis-Tris, alanine, acetate or even saline.

6. REFERENCES

The following literature citations as well as those cited above are incorporated in pertinent part by reference herein for the reasons cited in the above text:

Agre and Cartron, "Molecular Biology of the Rh Antigens," *Blood*, 78:551–563, 1991.

Anderson, "The Experimental Production of Erythroblastosis Foetalis in Rabbits," *Brit. J Haemat.*, 2:44–60, 1956.

Bang et al., "Ultrasound-Guided Fetal Intravenous Transfusion for Severe Rhesus Hemolytic Disease," *Brit. Med. J*, 284:373–374, 1982.

Berkowitz et al., "Intrauterine Intravascular Transfusions for Severe Red Blood Cell Isoimmunization: Ultrasound-Guided Percutaneous Approach," *Am. J Obstet. Gynecol.*, 155:574–581, 1986.

Carter, "Preliminary Reporter on a Substance Which Inhibits Anti-Rh Serum," *Am. J Clin. Path.*, 17:646–649, 1947.

Carter, "Rh Hapten: Its Preparation, Assay and Nature," *J. Immunol.*, 61:79–88, 1949.

Carter, "Preparation and Assay of a Red Cell Fraction of the Rh Factor," *Am. J Clin. Path.*, 21:561–565, 1951.

Carter, "A Survey of the Rh Hapten," *Texas Reports on Biol. and Med.*, 17:175–177, 1959.

Carter, "The Use of Rh Hapten in Prevention of Losses Due to Erythroblastosis Fetalis," *Proc. 7th Congress European Soc. Haematol., Part II*, 1215–1218, 1960.

Carter, "The Results in Clinical Use of Rh Hapten," *Am. J Ob. Gyn.*, 102:447–450, 1968.

Carter et al., "Evaluation of Rh Hapten," *Am. J Ob. Gyn.*, 72:655–659, 1956.

Carter and Lewis, "The Effects of Orally Administered Rh Hapten. A Study of 17 Cases," *Am. J. Ob. Gyn.*, 76:1286–1287, 1958.

Cohen, "The Immunogenetics of Cellular Antigen Systems of the Rabbit," In: *Oral Immunogenetics and Tissue Transplantation*, Eds. G. R. Riviere and W. H. Hildemann, Elsevier North Holland, Amsterdam, p. 183–197, 1982.

Cohen and Tissot, "Specialized Research Applications: II Serological Genetics," In: *The Biology of the Laboratory Rabbits*, Eds. S. H. Weisbroth, R. E. Flatt and A. L. Kraus, Academic Press, New York, p. 167–177, 1974.

Dippel, "The Prevention of Erythroblastosis Fetalis by the Use of Rh Hapten," *Southern Med. J*, 45:954–960, 1952.

Ehrenberg, "Report on Treatment of Obstetric Rh Isoimmunization with Hapten," *The Journal-Lancet*, 75:275–277, 1955.

Garner et al., "Prediction of the Severity of Haemolytic Disease of the Newborn," *Vox. Sang.*, 68:169–176, 1995.

Goldsmith, "Experiences with Rh Hapten," *Bull. Univ. Minnesota Hospitals and Minnesota Medical Foundation*, 20:188–194, 1948.

Goldsmith, "Experiences with Rh Hapten," *Wisconsin Med. J, May*, 1950.

Good and Izawa, *Meth. Enzymol.*, 24(B):53, 1972.

Grannum et al., "In Utero Exchange Transfusion in Severe Erythroblastosis Fetalis by Direct Intravascular Transfusion," *New Eng. J Med.*, 314:1431–1434, 1986.

Iyer et al., "Distribution of IgG Subtypes in Maternal Anti-D Sera and Their Prognostic Value in Rh Haemolytic Disease of the New-Born," *Acta Haematol.*, 88::78–81, 1992.

Kellner and Hedal, "Experimental Erythroblastosis Fetalis in Rabbits. I. Characterization of a Pair of Allelic Blood Group Factors and Their Specific Immune Isoantibodies," *J. Exp. Med*, 97:33–48, 1953.

Liley, "Intrauterine Transfusion of Foetus in Haemolytic Disease," *Brit Med. J.*, 2:1107–1109, 1963.

Moore et al., "Isolation of Membrane Components Associated with Human Red Cell Antigens Rh(D), (c), (E) and Fya," *Nature*, 295:529–531, 1982.

Paradis et al., "Protective Effect of the Membrane Skeleton on the Immunologic Reactivity of the Human Red Cell Rho(D) Antigen," *J. Immunol.*, 137:240–244, 1986.

Plapp et al., "Partial Purification of Rh(D) Antigen from Rh Positive and Negative Erythrocytes," *Proc. Natl. Acad. Sci USA*, 76:2964–2968, 1979.

Toupin and Carter, "Effect of Rh Hapten Ingestion on Serum Phospholipid," *Texas Reports on Biol. and Med.*, 19:370–375, 1961.

Wolf et al., "Study of Prevention of Erythroblastosis with Rh Hapten," *J. Am. Med. Assoc.*, 144:88–92, 1950.

Zaleski et al, *Immunogenetics*, Pitman Publishing, Boston, p. 242, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A method of detecting in a sample an antibody specific for a antigenically-active antigen, said method comprising:

(a) contacting said sample with a protein or peptide comprising an isolated and purified antienically-active Rh antigen protein or peptide, under conditions effective to allow the formation of an immune complex; and (b) detecting the immune complex so formed.

2. The method of claim 1, wherein said antibody is an anti-Rh antibody.

3. The method of claim 2, wherein said antibody is a human or rabbit antibody.

4. The method of claim 3, wherein said antibody is an anti-D antibody, an anti-c antibody, an anti-C antibody, an anti-e antibody, an anti-E antibody, an anti-A antibody, and anti-B antibody, or an anti-F antibody.

5. The method of claim 1, wherein said sample is a blood, serum, plasma, cerebrospinal fluid, lymph, synovial fluid, tissue sample, or culture supernatant.

6. The method of claim 1, wherein said protein or peptide is linked to a detectable label.

7. The antibody of claim 6, wherein said protein or peptide is linked to a radioactive label, a fluorogenic label, a nuclear magnetic spin resonance label, biotin or an enzyme that generates a colored product upon contact with a chromogenic substrate.

8. An immunodetection kit comprising, in suitable container means, a protein or peptide comprising an isolated and purified antigenically-active Rh antigen protein or peptide, and an immunodetection reagent.

9. The immunodetection kit of claim 8, wherein the immunodetection reagent is a detectable label that is linked to said protein or peptide.

10. The immunodetection kit of claim 9, wherein the immunodetection reagent is a detectable label that is linked to a second antibody that has binding affinity for said protein or peptide.

11. The immunodetection kit of claim 10, wherein the immunodetection reagent is a detectable label that is linked to a second antibody that has binding affinity for a human Rh blood group antigen protein or peptide.

12. The immunodetection kit of claim 10, wherein said Rh antigen is a D antigen, a c antigen, a C antigen, an e antigen, an E antigen, an A antigen, a B antigen, or an F antigen.

* * * * *

UNITED STATES PATENT AND TRADEMARK OFFICE
CERTIFICATE OF CORRECTION

PATENT NO. : 6,280,958 B1
DATED : August 28, 2001
INVENTOR(S) : Rodkey et al.

It is certified that error appears in the above-identified patent and that said Letters Patent is hereby corrected as shown below:

Column 50,
Line 14, please delete "a" and insert -- an -- therefor.
Line 14, please insert -- Rh -- between "antigenically-active" and "antigen".
Line 16, please delete "antienically-active "and insert -- antigenically-active -- therefor.
Line 26, please delete "and" and insert -- an -- therefor.
Line 29, please delete "." between "," and "lymph".

Signed and Sealed this

Thirtieth Day of April, 2002

Attest:

Attesting Officer

JAMES E. ROGAN
Director of the United States Patent and Trademark Office